United States Patent
Filiaggi et al.

(10) Patent No.: US 12,145,875 B2
(45) Date of Patent: Nov. 19, 2024

(54) POLYPHOSPHATE GLASS MICROSPHERES, METHODS OF MAKING AND USES THEREOF

(71) Applicant: Dalhousie University, Halifax (CA)

(72) Inventors: Mark Filiaggi, Bedford (CA); Arash Momeni, Halifax (CA)

(73) Assignee: Dalhousie University

( * ) Notice: Subject to any disclaimer, the term of this patent is extended or adjusted under 35 U.S.C. 154(b) by 740 days.

(21) Appl. No.: 15/762,790

(22) PCT Filed: Sep. 27, 2016

(86) PCT No.: PCT/CA2016/051129
§ 371 (c)(1),
(2) Date: Mar. 23, 2018

(87) PCT Pub. No.: WO2017/054076
PCT Pub. Date: Apr. 6, 2017

(65) Prior Publication Data
US 2018/0265402 A1    Sep. 20, 2018

Related U.S. Application Data

(60) Provisional application No. 62/233,646, filed on Sep. 28, 2015.

(51) Int. Cl.
*A61K 9/00* (2006.01)
*A61K 9/16* (2006.01)
(Continued)

(52) U.S. Cl.
CPC ............ *C03C 12/00* (2013.01); *A61K 9/0019* (2013.01); *A61K 9/1611* (2013.01); *A61K 9/501* (2013.01); *C03B 19/106* (2013.01); *C03C 1/006* (2013.01); *C03C 3/16* (2013.01); *C03C 4/0014* (2013.01); *C03C 4/0021* (2013.01); *C03B 2201/70* (2013.01); *C03C 2204/00* (2013.01)

(58) Field of Classification Search
CPC ..................................................... C03C 12/00
See application file for complete search history.

(56) References Cited

U.S. PATENT DOCUMENTS

| 3,946,130 A | 3/1976 | Tung et al. |
| 4,089,932 A | 5/1978 | Morita et al. |

(Continued)

FOREIGN PATENT DOCUMENTS

| CA | 2438108 A1 | 8/2002 |
| JP | 61-205636 A | 9/1986 |
| WO | 00/44681 A3 | 8/2000 |

OTHER PUBLICATIONS

Arshady, Microspheres and Microcapsules, a Survey of Manufacturing Technique Part II: Coaveration, Polymer Engineering and Science, 1990, vol. 30 (15), 905-914.*

(Continued)

*Primary Examiner* — Paul W Dickinson
(74) *Attorney, Agent, or Firm* — Smart & Biggar LP; Luba Naiberger

(57) ABSTRACT

Polyphosphate glass microspheres (PGMs) are prepared using a polyphosphate coacervate. PGMs can be loaded with various therapeutic agents and can be used for various medical and dental procedures and treatments.

8 Claims, 12 Drawing Sheets

(51) Int. Cl.
*A61K 9/50* (2006.01)
*C03B 19/10* (2006.01)
*C03C 1/00* (2006.01)
*C03C 3/16* (2006.01)
*C03C 4/00* (2006.01)
*C03C 12/00* (2006.01)

(56) References Cited

U.S. PATENT DOCUMENTS

| | | | |
|---|---|---|---|
| 4,789,501 | A | 12/1988 | Day et al. |
| 5,713,974 | A | 2/1998 | Martin et al. |
| 6,210,715 | B1 | 4/2001 | Starling et al. |
| 6,358,531 | B1 | 3/2002 | Day et al. |
| 8,865,123 | B1 | 10/2014 | Day et al. |
| 2002/0004111 | A1 | 1/2002 | Matsubara et al. |

OTHER PUBLICATIONS

Alexandrino et al., "Paclitaxel-loaded polyphosphate nanoparticles: a potential strategy for bone cancer treatment", Journal of Materials Chemistry B, 2(10):1298-1306, 2014.
Bohner et al., "Synthesis of spherical calcium phosphate particles for dental and orthopedic applications", Biomatter, 3:2:25103, 2013.
De Oliveira et al., "Amorphous manganese polyphosphates: preparation, characterization and incorporation of azo dyes", Journal of Sol-Gel Science and Technologies, 50:158-163, 2009.
Donovan et al., "Size-Controlled Synthesis of Granular Polyphosphate Nanoparticles at Physiological Salt Concentrations for Blood Clotting", Biomacromolecules, 15:3976-3984, 2014.
Franco et al., "Preparation and structural characterization of sodium polyphosphate coacervate as a precursor for optical materials", Materials Chemistry and Physics, 180:114-121, 2016.
Hum and Boccaccini, "Bioactive glasses as carriers for bioactive molecules and therapeutic drugs: a review", Journal of Materials Science: Materials in Medicine, 23:2317-2333, 2012.
Kim et al., "In situ fabrication of alendronate-loaded calcium phosphate microspheres: controlled release for inhibition of osteoclastogenesis", Journal of Controlled Release, 147(1):45-53, 2010.
Lakhkar et al., "Chapter 5: Titanium Phosphate Glass Microspheres as Microcarriers for In Vitro Bone Cell Tissue Engineering", RSC Smart Materials, 10:105-132, 2014.
Miyazaki et al., "Yttrium phosphate microspheres with enriched phosphorus content prepared for radiotherapy of deep-seated cancer", Ceramics International, 40(9)(Part B):15259-15263, 2014.
Momeni and Filiaggi, "Synthesis and characterization of different chain length sodium polyphosphates", Journal of Non-Crystalline Solids, 382:11-17, 2013.
Momeni and Filiaggi, "Comprehensive Study of the Chelation and Coacervation of Alkaline Earth Metals in the Presence of Sodium Polyphosphate Solution", Langmuir, 30(18):5256-5266, 2014.
Momeni and Filiaggi, "Room-Temperature Preparation of Phosphate Glass Microspheres as Carriers for Therapeutic Agents", 10th World Biomaterials Congress, Montréal, Canada, May 2016.
Momeni et al., "Developing an in situ forming polyphosphate coacervate as a new liquid embolic agent: From experimental design to pilot animal study", Acta Biomaterialia, 32:286-297, 2016.
Momeni and Filiaggi, "Degradation and hemostatic properties of polyphosphate coacervates", Acta Biomaterialia, 41:328-341, 2016.
Momeni and Filiaggi, "Rheology of polyphosphate coacervates", Journal of Rheology, 60(1):25-34, 2016.
Müller et al., "Retinol encapsulated into amorphous Ca(2+) polyphosphate nanospheres acts synergistically in MC3T3-E1 cells", European Journal of Pharmaceutics and Biopharmaceutics, 93:214-223, 2015.
Palavit et al., "Preparation of zinc-sodium phosphate glass precursors by coacervation", Journal of Non-Crystalline Solids, 189:277-282, 1995.
PCT International Search Report, PCT/CA2016/051129, dated Dec. 6, 2016 (4 pages).
Perez et al., "Therapeutic bioactive microcarriers: Co-delivery of growth factors and stem cells for bone tissue engineering", Acta Biomaterialia, 10:520-530, 2014.
Pickup et al., "Sol-Gel Phosphate-based Glass for Drug Delivery Applications", Journal of Biomaterials Applications, 26:613-622, 2012.
Pickup et al., "Characterisation of phosphate coacervates for potential biomedical applications", Journal of Biomaterials Applications, 28(8):1226-1234, 2014.
Sene et al., "Synthesis and characterization of phosphate glass microspheres for radiotherapy applications", Journal of Non-Crystalline Solids, 354(42-44):4887-4893, 2008.
Willot et al., "Preparation of zinc sodium polyphosphates glasses from coacervates precursors. Characterisation of the obtained glasses, and their applications", C. R. Chimie, 5:899-906, 2002.
Zhou et al., "Preparation of calcium phosphates with negative zeta potential using sodium calcium polyphosphate as a precursor", Materials Letters, 156:79-81, 2015.
El-Damrawi et al., "Structural Studies on Ag2O-P2O5 Glasses", New Journal of Glass and Ceramics, 2017, 7, 77-89.
Onyiriuka, "Zinc phosphate glass surfaces studied by XPS", Journal of Non-Crystalline Solids, 163 (1993) 268-273.
Alhasni, "Insight into the structure of magnesium and sodium mixed phosphate glasses: A molecular dynamics study", Journal of Non-Crystalline Solids, 578 (2022) 121338.
Larink et al., "Mixed Network Former Effect in Ion-Conducting Alkali Borophosphate Glasses: Structure/Property Correlations in the System [M2O]1/3[(B2O3)x(P2O5)1-x]2/3 (M = Li, K, Cs)", J. Phys. Chem. C, 2012, 116, 26162-26176.
Du et al., "Structure of Cerium Phosphate Glasses: Molecular Dynamics Simulation", J. Am. Ceram. Soc., 94 [8] 2393-2401, 2011.
Christie et al., "Nanoscale Chains Control the Solubility of Phosphate Glasses for Biomedical Applications", J. Phys. Chem. B 2013, 117, 10652-10657.
Brow et al., "Cation Effects on 31P MAS NMR Chemical Shifts of Metaphosphate Glasses", J. Am. Ceram. Soc., 74 [6] 1287-90, 1991.
Arai et al., "Aluminum or phosphorus co-doping effects on the fluorescence and structural properties of neodymium- doped silica glass", J. Appl. Phys. 59 (10), May 15, 1986.
Moeller, "Phosphorus and Its Compounds", J. Am. Chem. Soc., vol. 1: Chemistry., pp. 430-434, 81, 11, 2916, Jun. 1, 1959.

* cited by examiner

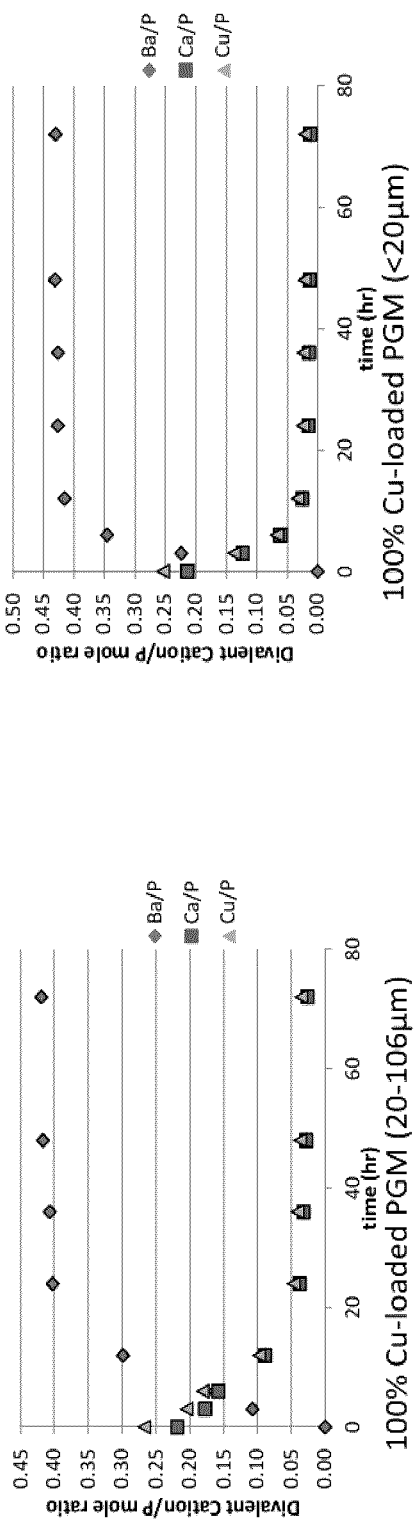
FIG. 11B
FIG. 11A
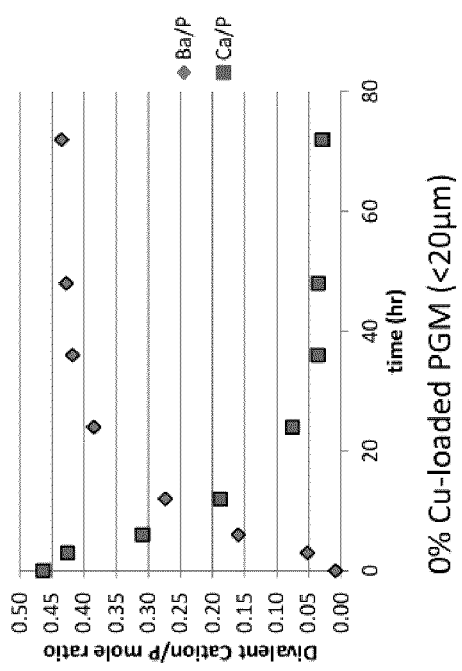
FIG. 11D
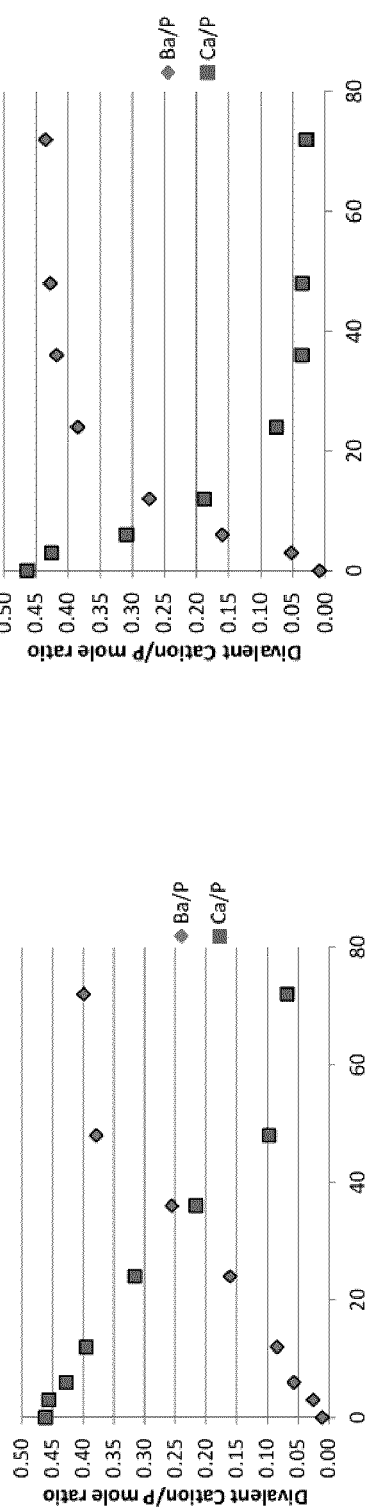
FIG. 11C

FIG. 12E
FIG. 12F
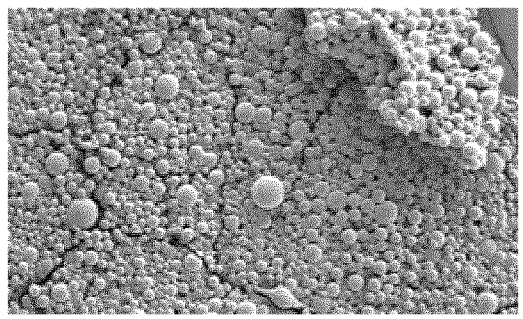
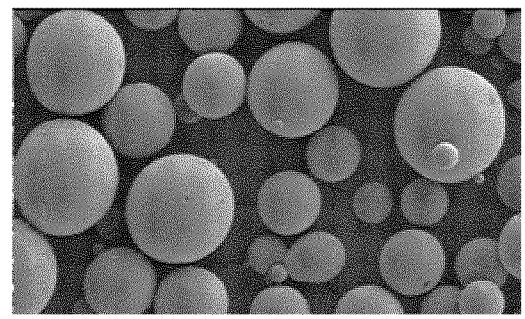
FIG. 13A
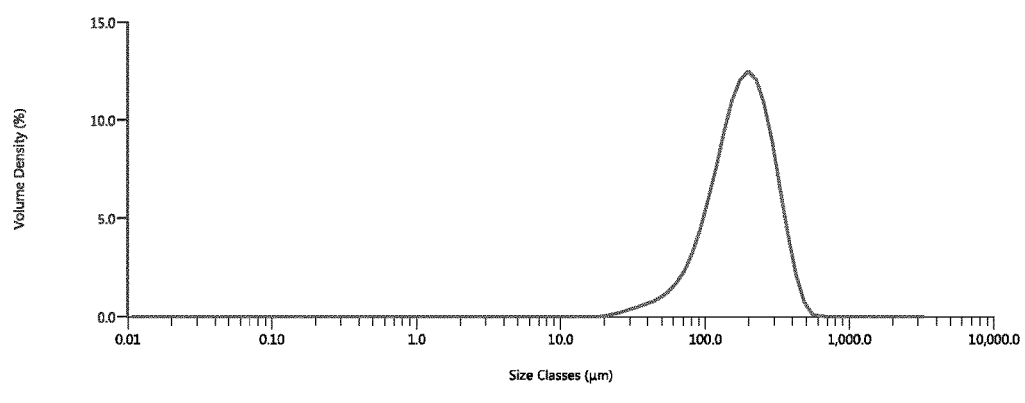
FIG. 13B
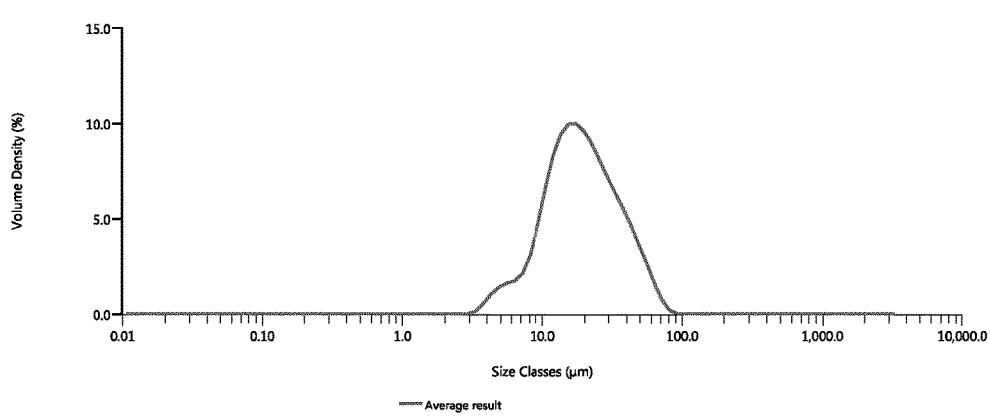

POLYPHOSPHATE GLASS MICROSPHERES, METHODS OF MAKING AND USES THEREOF

CROSS-REFERENCE TO RELATED APPLICATIONS

This application claims the benefit of and priority under 35 U.S.C. § 371 to Patent Cooperation Treaty application PCT/CA2016/051129, filed Sep. 27, 2016, which claims the benefit of U.S. Provisional Application Ser. No. 62/233,646, filed Sep. 28, 2015, the entire contents of both disclosures, which are incorporated herein by reference in their entireties.

TECHNICAL FIELD OF THE INVENTION

The present invention relates to processes and compositions for the preparation of polyphosphate glass microspheres (PGM) using polyphosphate coacervates as precursor comprised of (1) polyphosphates with average degree of polymerization between 3-20,000, and (2) cations including divalent, trivalent and higher valency cations.

BACKGROUND

The statements in this section merely provide background information related to the present disclosure and may not constitute prior art.

Polymeric microspheres are widely accepted as carriers for therapeutic agents due to their excellent biocompatibility and biodegradability, however they lack osteoconductivity and mechanical stiffness which glass microspheres could offer in dental or bone-related applications. Currently glass microspheres are only prepared by high temperature processing methods (e.g. propane torch method). However, therapeutic agents cannot be loaded into such glasses because of the high temperature involved. Irregularly-shaped glass particles can be prepared by sol-gel methods (e.g. mesoporous glasses). These glasses can be loaded by direct addition of the therapeutic agent to the sol or by subsequent soaking of the glass in the therapeutic agent solution. However these methods result in low encapsulation efficiency, glass particles that are irregular in shape and generally highly brittle due to their porous structure.

Thus, there exists a need in the art for new and improved methods for making biocompatible, resilient, osteoconductive dental and orthopedic materials employing polyphosphate glass microspheres. The present invention addresses this need.

SUMMARY

The following only summarizes certain aspects of the invention and is not intended to be limiting in nature. These aspects and other aspects and embodiments are described more fully below. All references cited in this specification are hereby incorporated by reference in their entirety. In the event of a discrepancy between the express disclosure of this specification and the references incorporated by reference, the express disclosure of this specification shall control.

In a first aspect, the present invention provides a method for the synthesis of polyphosphate glass microspheres (herein after referred to as "PGMs") and their use in biomedical applications. In one embodiment, a method for making PGMs include: (a) providing a phosphate polymer comprising a linear polymer of phosphate having a degree of polymerization (Dp) ranging from about 3 to about 20,000; (b) preparing a coacervate comprising admixing an aqueous solution of phosphate polymer with cations thereby forming a polyphosphate coacervate has a $M^z/P$ mole ratio equal to (1/z), where z represents the valency of the cation; (c) admixing the polyphosphate coacervate with a water immiscible organic solvent to transform the polyphosphate coacervate into spherical particles; and (d) solidifying the spherical particles using a solvent extraction process, a solvent evaporation process or a spray drying process, to form the polyphosphate glass microspheres. In some embodiments, methods for making the PGMs may optionally also include step (e) dehydrating the polyphosphate glass microspheres by admixing the polyphosphate glass microspheres of step (d) with a water immiscible solvent. Accordingly, the present invention provides various methods for the synthesis of PGMs using a polyphosphate coacervate.

In some embodiments, the methods for preparing PGMs loaded with a therapeutic agent comprises preparing a polyphosphate coacervate, admixing the polyphosphate coacervate with a therapeutic agent to form a polyphosphate coacervate mixture, dispersing the polyphosphate coacervate mixture in a liquid, and isolating the polyphosphate glass microspheres using a solvent. Optionally, the polyphosphate glass microspheres are sedimented or collected to remove excess solvent and washed one more time.

In a second aspect, the present invention provides PGMs containing a polyphosphate and cation coascervate, wherein the polyphosphate coacervate has a $M^z/P$ mole ratio equal to (1/z), where z represents the valency of the cation. The phosphate polymer in the PGMs have a degree of polymerization (Dp) ranging from about 3 to about 20,000. In various embodiments, the PGMs of the present invention have a therapeutic agent contained within the PGM, uniformly distributed and is able to be released in a controlled manner. Furthermore, the PGMs of the present invention can have a therapeutic agent loaded within the PGM that is active and stable when released from the PGM under conditions that promote release of the therapeutic agent from the PGMs. In some embodiments, the therapeutic agent can include: a drug, a medicament, a pharmaceutical agent including a disinfecting agent, e.g. an antimicrobial agent, an anti-inflammatory agent, a vaccine, an anti-tumor agent, a drug, radioactive or non-radioactive contrasting agents, or a natural product such as ions, (e.g. monovalent, divalent or trivalent cations or anions, e.g. Cu or Ag ions) or a biologically active agent, for example, a biological growth factor, a peptide, a polypeptide, a protein, a lipid, or a nucleic acid. Advantageously, the PGMs of the present invention are made from a polyphosphate/cation coacervate that enables incorporation of the therapeutic agent in a non-destructive manner that preserves the activity of the therapeutic agent when administered and released from the PGMs. In some embodiments, the activity of the therapeutic agent when released from the PGMs is at least 50%, or at least 60%, or at least 70%, or at least 80%, or at least 90%, or at least 95%, or at least 99% when compared to the same amount of therapeutic agent not encapsulated into PGMs of the present invention, when tested either in vitro, or in vivo.

In a related aspect, the present invention provides methods for the treatment of various medical and dental disorders and conditions by administering a therapeutically effective amount to the subject in need thereof to treat the medical and dental disorders and conditions.

BRIEF DESCRIPTION OF THE DRAWINGS

The drawings described herein are for illustration purposes only and are not intended to limit the scope of the present disclosure in any way.

FIG. 11A depicts a graph studying the replacement of Ca and Cu with Ba during the ion-exchange process and its dependence on the 100% Cu loaded PGM size of 20-106 μm.

FIG. 11B depicts a graph studying the replacement of Ca and Cu with Ba during the ion-exchange process and its dependence on the 100% Cu loaded PGM size of <20 μm.

FIG. 11C depicts a graph studying the replacement of Ca and Cu with Ba during the ion-exchange process and its dependence on the 0% Cu loaded PGM size of 20-106 μm.

FIG. 11D depicts a graph studying the replacement of Ca and Cu with Ba during the ion-exchange process and its dependence on the 0% Cu loaded PGM size of <20 μm.

FIG. 12E depicts a SEM photomicrograph of small minocycline loaded calcium polyphosphate microspheres at various magnifications.

FIG. 12F depicts a SEM photomicrograph of large minocycline loaded calcium polyphosphate microspheres at various magnifications.

FIG. 13A depicts a particle size distribution curve for large minocycline loaded calcium polyphosphate microspheres using laser diffraction (Malvern Mastersizer 3000).

FIG. 13B depicts a particle size distribution curve for small minocycline loaded calcium polyphosphate microspheres using laser diffraction (Malvern Mastersizer 3000).

DETAILED DESCRIPTION OF THE EMBODIMENTS

Figure 1:
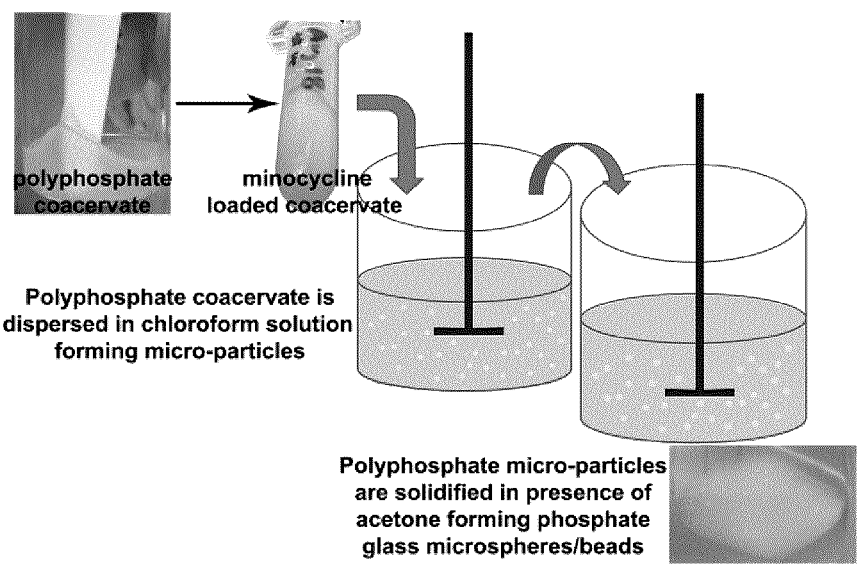
FIG. 1. depicts a schematic representation of the synthesis process for making PGMs loaded with the antibiotic minocycline.

The following set of definitions is merely exemplary in nature and is not intended to limit the present disclosure, application, or uses.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested. The following definitions and non-limiting guidelines must be considered in reviewing the description of the technology set forth herein.

The headings (such as "Introduction" and "Summary") and sub-headings used herein are intended only for general organization of topics within the present technology, and are not intended to limit the disclosure of the present technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The citation of references herein does not constitute an admission that those references are prior art or have any relevance to the patentability of the technology disclosed herein. Any discussion of the content of references cited in the Introduction is intended merely to provide a general summary of assertions made by the authors of the references, and does not constitute an admission as to the accuracy of the content of such references. All references cited in the "Description" section of this specification are hereby incorporated by reference in their entirety.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9.

Although the open-ended term "comprising," as a synonym of terms such as including, containing, or having, is used herein to describe and claim the present invention, the invention, or embodiments thereof, may alternatively be described using more limiting terms such as "consisting of" or "consisting essentially of" the recited ingredients.

As used herein, a therapeutic agent is an active agent that may be used to prevent a disease or a symptom thereof, to treat a disease, disorder, malady or any symptom related thereof. The term "therapeutic agent" is used in its broadest sense and includes any substance or mixture of substances that provides clinical use. A therapeutic agent could be any agent which provides a therapeutic or prophylactic effect, a compound that affects or participates in tissue growth, cell growth, cell differentiation, a compound that may be able to invoke a biological action such as an immune response, or could play any other role in one or more biological processes. The phrase "therapeutic agent(s)" refers to a number of different drugs, medicaments, pharmaceutically active agents, biologically active agents available or, as well as future agents that can be useful. The therapeutic agent component can take a number of different forms including anti-microbials, anti-infective agents, germicides, anti-septics, anti-oxidants, anti-inflammatory agents, anti-coagulant agents, drugs to alter lipid metabolism, anti-proliferatives, anti-neoplastics, tissue growth stimulants, functional protein/factor delivery agents, imaging agents, radionuclides, anti-imaging agents, anesthetic agents, tissue absorption enhancers, anti-adhesion agents, analgesics, prodrugs, and analogs or derivatives thereof and any additional desired therapeutic agents.

As used herein, the term "biologically active agent" or "bioactive agent" means an agent that is capable of providing a local or systemic biological, physiological, or therapeutic effect in the biological system to which it is applied. In some illustrative and non-limiting examples, the bioactive agent is a disinfecting agent, a growth factor, a pharmaceutically active agent, a peptide, polypeptide, a lipid or a nucleic acid.

In some aspects, the bioactive agent is an osteogenic growth factor. In some aspects, the bioactive agent is osteoinductive. Osteoinductive examples include but are not limited to transforming growth factors (TGFs), bone morphogenetic proteins (BMPs), fibroblast growth factors (FGFs), parathyroid hormone derivatives (PTHs), Nell-1, statins, certain known osteoinductive peptides (e.g., P15, truncated PTHs or collagens), insulin-like growth factors (IGFs), and/or platelet-derived growth factors (PDGFs), or their respective therapeutic nucleotide transgenes.

As used herein, the term "pharmaceutically active agent" includes a "drug" or a "medicament" and means a molecule, group of molecules, complex or substance administered to an organism for diagnostic, therapeutic, preventative medical, or veterinary purposes. In the context of the disclosed combination biomaterials this term includes internally administered topical or locally released, and systemic human and animal pharmaceuticals, treatments, remedies, nutraceuticals, cosmeceuticals, biologicals, biomaterials, diagnostics and contraceptives, including preparations useful in clinical and veterinary screening, prevention, prophylaxis, healing, wellness, detection, imaging, diagnosis, therapy, surgery, monitoring, cosmetics, prosthetics, forensics and the like. This term includes, but is not limited to, RNAi technologies and reagents, transgenes, protein growth factors, antimicrobials, antibiotics, microcidals, antiseptics, antifungals, antiinflammatories, anesthetics, and analgesics. This term may also be used in reference to agriceutical, workplace, military, industrial and environmental therapeutics or remedies comprising selected molecules or selected nucleic acid sequences capable of recognizing cellular receptors, membrane receptors, hormone receptors, therapeutic receptors, microbes, viruses or selected targets comprising or capable of contacting plants, animals and/or humans. This term can also specifically include nucleic acids and compounds comprising nucleic acids that produce a bioactive effect, for example deoxyribonucleic acid (DNA) or ribonucleic acid (RNA) as genetic materials introduced to produce a desired therapeutic effect.

The terms "drug", "biologically active agent" or "bioactive agent" also includes the herein disclosed categories and specific examples. It is not intended that the category be limited by the specific examples. Those of ordinary skill in the art will recognize also numerous other compounds that fall within the categories and that are useful according to the invention.

As used herein, the term "osteoinduction" refers to the ability to stimulate the proliferation and differentiation of progenitor and partially differentiated cell types involved in initiating and completing bone formation and its tissue regeneration, including, but not limited to, exogenous pluripotent cells, mesenchymal MSC, satellite-derived musculoskeletal SDMSC, adipose-derived ADSC, induced pluripotent (iPS), and endogenously sourced stem cells (including MSCs, ADSC, SDMSC, both circulating and tissue resident). In endochondral bone formation, stem cells differentiate into chondroblasts and chondrocytes, laying down a cartilaginous ECM, which subsequently calcifies and is remodeled into lamellar bone. In intramembraneous bone formation, the stem cells differentiate directly into osteoblasts, which form bone through direct endogenous mechanisms. Direct recruitment of other differentiated cell types involved in bone formation is also significant to healing, including differentiated microvascular and endothelial cells, mural cells and pericytes, osteoblasts, chondrocytes, chondroblasts, osteoclasts, and osteocytes. Osteoinduction can be stimulated by osteogenic growth factors such as those mentioned above, although some ECM proteins also drive progenitor cells toward the osteogenic phenotype.

As used herein, the term "osteoconduction" refers to the ability to stimulate the attachment, migration, and distribution of vascular and osteogenic cells within and in contact with the PGMs. The physical characteristics that affect the graft's osteoconductive activity include porosity, pore size, and three-dimensional architecture. In addition, direct biochemical interactions between matrix proteins and cell surface receptors play a major role in the host's response to the graft material and ability to produce effective therapies in these sites.

As used herein, the term "osteogenic" refers to the intrinsic ability of a combination biomaterial to produce bone in the host site. To have direct osteogenic activity, the combination biomaterial substrate can contain or elicit cellular components that directly induce bone formation and regeneration. For example, an implanted collagen matrix pre-seeded with activated MSCs would have the potential to induce bone formation directly, without recruitment and activation of host MSC populations. Because many osteoconductive scaffolds also have the ability to bind and deliver bioactive molecules, their osteoinductive potential will be greatly enhanced. Therefore combinations of osteoconductive and osteoinductive materials and agents can be used for bone regenerative purposes with the combination biomaterial, the combination biomaterial substrate or the degradable polymer.

Polyphosphates as used herein are salts or esters of polymeric oxyanions formed from phosphate structural units linked together by sharing oxygen atoms. PGM comprised of polyphosphates and any cation can be prepared as long as a polyphosphate coacervate of that cation can be prepared. The term coacervation is defined as the separation of a polymeric solution into two liquid phases, with the liquid phase of higher viscosity representing the coacervate. The coacervation of polyphosphate in the presence of cations (for example, $Ag^+$, $Zn^{2+}$, $Tc^{4+}$, $Gd^{3+}$, $Ga^{3+}$, $La^{3+}$, $Ca^{2+}$, $Cu^{2+}$, $Mg^{2+}$, $Sr^{2+}$, $Fe^{2+}$, $Y^{3+}$, $Ba^{2+}$ or combinations thereof) is governed principally by hydrophobic and electrostatic forces. In one exemplary embodiment, a solution of polyphosphate can be prepared by dissolving monovalent polyphosphate salts (e.g. sodium polyphosphate (NaPP)) or polyphosphoric acids. Polyphosphate coacervates can be obtained if cations with small ionic size are used (e.g. $Ca^{2+}$, $Y^{3+}$). If large size cations are used such as $Ba^{2+}$, a polyphosphate coacervate cannot be obtained unless a combination of this large cation is used along with smaller cations. For instance, if $BaCl_2$ alone is added to a NaPP solution a flocculate is obtained which cannot be used for PGM preparation. In contrast, if a combination of $BaCl_2$ and $CaCl_2$ (30:70 Ba:Ca mole ratio) is used, a coacervate can be obtained and can be used for PGM preparation. The degree of polymerization (number of phosphate units per polymer) of the polyphosphate being used is also important. For instance, a coacervate with $BaCl_2$ and $CaCl_2$ (30:70 Ba:Ca mole ratio) cannot be obtained if the polyphosphate has degree of polymerization of 20, but if it has degree of polymerization of 200 a coacervate can be obtained. PGMs can be prepared for polyphosphates with a Dp between 3-20,000. Even if a polyphosphate coacervate of a desired cation cannot be prepared, one can still obtain PGM of that cation using an additional ion-exchange process which will be described herein.

As described above preparation of PGM of a specific cation requires first that the polyphosphate coacervate of that cation is prepared. Exemplary methods are provided to illustrate the preparation of Ca & Cu polyphosphate coacervates and their use in the synthesis of their corresponding PGMs.

A. Methods for Producing Phosphate Glass Microspheres Using Polyphosphate Coacervates The first step in the development of polyphosphate microspheres is the formation of a coacervate. To prepare such a coacervate, in some embodiments, we start from sodium polyphosphate (NaPP) glass. Other commonly known names for (NaPP) glass include: Graham salt, sodium hexametaphosphate, and sodium polymetaphosphate. NaPP is prepared as described in [Momeni, A., and Filiaggi, M. J., "Synthesis and characterization of different chain length sodium polyphosphates," Journal of Non-Crystalline Solids 382, 11-17 (2013) the disclosure of which is incorporated herein by reference in its entirety]. This glass is water-soluble and is comprised of mainly polyphosphate polymer, which is a linear polymer made of phosphate groups that are bound together through P—O—P bonds. Longer chains with degree of polymerization (Dp) (i.e. number of phosphate groups per chain) higher than 500 can be produced by an ion exchange process of crystalline polyphosphate phases such as potassium Kurrol salt, as described in [Momeni, A., and Filiaggi, M. J., "Synthesis and characterization of different chain length sodium polyphosphates," Journal of Non-Crystalline Solids 382, 11-17 (2013)]. When excess divalent, or trivalent cations ($M^{II}$) for example, $Ag^+$, $Zn^{2+}$, $Tc^{4+}$, $Gd^{3+}$, $Ga^{3+}$, $La^{3+}$, $Ca^{2+}$, $Cu^{2+}$, $Mg^{2+}$, $Sr^{2+}$, $Fe^{2+}$, $Y^{3+}$, $Ba^{2+}$ or combinations thereof, are added to an aqueous solution of polyphosphate, a phase separation occurs resulting in formation of coacervate or flocculate depending on the $M^{II}$ type; only polyphosphate coacervate is useful for microsphere preparation. Coacervate is a highly viscous liquid phase that separates from the original solution and is comprised mainly of MII, polyphosphate, and a limited volume of water as depicted graphically in FIG. 1.

To prepare polyphosphate coacervates, NaPP—preferably with a Dp less than 100—is dissolved in deionized water, preferably at phosphate concentration lower than 1% (g/mL). Other monovalent polyphosphates (e.g. potassium polyphosphate or lithium polyphosphate) or polyphosphoric acids may also be used. Then a $M^{II}$ solution, preferably 1 M $CaCl_2$, or $CuCl_2$, or $BaCl_2$, or combinations thereof is added to the NaPP solution to reach $M^{II}/P$ mole ratio of at least 0.5. In case a specific cation (e.g. antibacterial $Cu^{2+}$) is required to be loaded into the final PGMs, it will be added here in addition to the Ca solution. After $M^{II}$ addition, the NaPP solution immediately becomes cloudy and a liquid coacervate layer forms at the bottom of the beaker. Depending on the phosphate concentration and Dp, a centrifuge step might also be required. The polyphosphate coacervate is collected, washed 3 times with deionized water, and is used in the following steps. Polyphosphate coacervates may be prepared using a variety of cations including both organic (e.g. amine compounds such as spermine, polyimine, chitosan, etc.) and inorganic cations (e.g. $Ag^+$, $Zn^{2+}$, $Tc^{4+}$, $Gd^{3+}$, $Ga^{3+}$, $La^{3+}$, $Ca^{2+}$, $Cu^{2+}$, $Mg^{2+}$, $Sr^{2+}$, $Fe^{2+}$, $Y^{3+}$, $Ba^{2+}$ or combinations thereof)

Step 2—Therapeutic Agent Loading into Polyphosphate Coacervate

Where a therapeutic agent is required to be loaded into the final microspheres, it will be added to the coacervate. The therapeutic agent can be added as a powder and then dispersed evenly throughout the coacervate by mixing. Alternatively, the therapeutic agent can be dissolved in water and then added to the coacervate followed by mixing. The coacervate can also be freeze-dried and then the therapeutic agent (in powder or solution) can be added to the coacervate. Enough time should be given for the mixing in order to get the therapeutic agent homogenously distributed throughout the coacervate and the mixing should be preferably carried out at low temperature (e.g. at about 4° C.). As an example, minocycline HCl, an antibiotic agent, can be loaded into the coacervate by first freeze drying 2 g of the coacervate and then adding 1.5 mL of a 13 mg/mL minocycline solution to the freeze-dried coacervate. This mixture is kept at about 4° C. and mixed overnight and the resulting coacervate completely absorbs the yellow colored drug as shown in FIG. 1. This coacervate is used in microsphere preparation as described below. In some embodiments, the therapeutic agent can include one or more agents including: a pharmaceutically active agent, a drug, a medicament, a biologically active agent, or a bioactive agent. In various embodiments, an illustrative therapeutic agent can include an anti-infective agent, an antimicrobial agent, a disinfecting agent, anti-inflammatory agents, chemotherapeutic agents, antibodies, and contrasting agents for diagnostic imaging, whether using radiotherapy or non-radiotherapy imaging techniques. As used herein, disinfecting agents can include bacteriostatic agents, antimicrobials, microbicidals, antibiotics, antivirals, antifungals, antimalarials, anthelmintics, antiprotazoan agents, and generally any agent whether synthetic or naturally occurring that is able to inhibit the growth of a microorganism, i.e. a bacterium, a virus, a fungus, a helminth, a protozoan and the like.

In some embodiments, illustrative therapeutic agents that may be used with the PGMs of the present invention include disinfecting agents such as an antimicrobial agent: (i) cephalosporins such as cephalexin, cefoxytin and cephalothin; (ii) penicillins such as amoxycillin, amoxycillin with clavulanic acid, ampicillin, bacampicillin, benzathine penicillin, benzylpenicillin, carbenicillin, cloxacillin, methicillin, phenethicillin, phenoxymethylpenicillin, flucloxacillin, mezlocillin, piperacillin, ticarcillin and azlocillin; (iii) tetracyclines such as minocycline, chlortetracycline, tetracycline, demeclocycline, doxycycline, methacycline and oxytetracycline and other tetracycline-type antibiotics; (iv) minoglycosides such as amikacin, gentamicin, kanamycin, neomycin, netilmicin and tobramycin. Antifungals such as amorolfine, isoconazole, clotrimazole, econazole, miconazole, nystatin, terbinafine, bifonazole, amphotericin, griseofulvin, ketoconazole, fluconazole and flucytosine, salicylic acid, fezatione, ticlatone, tolnaftate, triacetin, zinc, pyrithione and sodium pyrithione; (v) Quinolones such as nalidixic acid, cinoxacin, ciprofloxacin, enoxacin and norfloxacin. Sulphonamides such as phthalylsulphthiazole, sulfadoxine, sulphadiazine, sulphamethizole and sulphamethoxazole; (vi) Sulphones such as dapsone; and (vii) Other miscellaneous antibiotics such as chloramphenicol, clindamycin, erythromycin, erythromycin ethyl carbonate, erythromycin estolate, erythromycin glucepate, erythromycin ethylsuccinate, erythromycin lactobionate, roxithromycin, lincomycin, natamycin, nitrofurantoin, spectinomycin, vancomycin, aztreonam, colistin IV, metronidazole, tinidazole, fusidic acid and trimethoprim; 2-thiopyridine N-oxide; halogen compounds, particularly iodine and iodine compounds such as iodine-PVP complex and diiodohydroxyquin; hexachlorophene; chlorhexidine; chloroamine compounds; benzoylperoxide (viii) Anti-tuberculosis drugs such as ethambutol, isoniazid, pyrazinamide, rifampicin and clofazimine. Antimalarials such as primaquine, pyrimethamine, chloroquine, hydroxychloroquine, quinine, mefloquine and halofantrine, (ix) Antiviral agents such as acyclovir and acyclovir prodrugs, famciclovir, zidovudine, didanosine, stavudine, lamivudine, zalcitabine, saquinavir, indinavir, ritonavir, n-docosanol, tromantadine and idoxuridine, (x) Anthelmintics such as mebendazole, thiabendazole, niclosamide, praziquantel, pyrantel embonate and diethylcarbamazine (xi) alkyl parabens, such as methylparaben, ethylparaben, propylparaben, and butylparaben, cresol, chlorocresol, hydroquinone, sodium benzoate, potassium benzoate, triclosan, chlorhexidine, silver ion agents and silver-based compositions.

Other examples of therapeutic agents that can be encapsulated and added to the PGMs of the present invention can include growth factors, cytokines, chemokines, interleukins, and bone morphogenetic proteins (BMPs). In some embodiments, the therapeutic agent(s) can be osteoinductive, and/or promote regeneration and growth of tissue such as bone, cartilage, muscle, fat and the like, or can promote wound healing. It is understood that proteins such as growth factors can be naturally sourced or recombinant. In some aspects, the bioactive agent comprises a transforming growth factor (TGF). Thus, in some aspects, the bioactive agent comprises TGF-β1, TGF-β2, or TGF-β3. In some aspects, the bioactive agent comprises a bone morphogenetic protein (BMP). Thus, in some aspects, the bioactive agent comprises BMP-2, BMP-4, BMP-6, BMP-7, BMP-13. In some aspects, the bioactive agent comprises a fibroblast growth factor (FGF). In some aspects, the bioactive agent comprises an insulin-like growth factor (IGF). Thus, in some aspects, the bioactive agent comprises IGF-I, IGF-II. In some aspects, the bioactive agent comprises a platelet-derived growth factor (PDGF). Thus, in some aspects, the bioactive agent comprises PDGF-BB. In some aspects, the bioactive agent comprises a vascular endothelial growth factor (VEGF) or its bioactive recombinant fragments. In some aspects, the bioactive agent comprises Bone-derived growth factor-2 (BDGF II). In some aspects, the bioactive agent comprises LIM mineralization protein (LMP-1). In some aspects, the bioactive agent comprises growth differentiation factor 5 (GDF-5). In some aspects, the bioactive agent comprises parathyroid hormone derivatives (PTH). In some aspects, the therapeutic agent is an antimicrobial; a bioactive agent selected from the group consisting of a bone morphogenetic protein (BMP); TGF-β1, TGF-β2, TGF-β3; clotting factors (fibrinogen, prothrombin, tissue factor, calcium ions, proaccelerin, accelerin, proconvertin, antihaemophilic factor, christmas factor, stuart factor, plasma prothromboplastin antecedent, hageman factor and fibrin-stabilizing factor); fibroblast growth factor (FGF); insulin-like growth factor (IGF); platelet-derived growth factor (PDGF); vascular endothelial growth factor (VEGF); Bone-derived growth factor-2 (BDGF II); LIM mineralization protein (LMP-1); growth differentiation factor 5 (GDF-5); parathyroid hormone derivatives (PTH); an analgesic; an anthracycline; and combinations thereof.

Step 3—Formation of Phosphate Glass Microspheres

To form PGMs from the coacervate, the coacervate can be initially dispersed in an organic solvent that is immiscible with water during which the surface tension will transform the coacervate to spherical particles. Subsequently, these particles are solidified using a solvent extraction method by the addition of a water-miscible solvent that is also miscible with the first organic solvent. There are other methods that could be used to solidify these particles including solvent evaporation techniques or spray drying techniques. These resulting PGMs are collected after centrifugation and several washing steps in an appropriate solvent (water-immiscible solvents such as chloroform or dichloromethane and water-miscible solvents such as acetone or alcohols). Following is an exemplary method for microsphere synthesis by an established route: 9 g of polycaprolactone (PCL) as a thickening agent is dissolved in 150 mL chloroform followed by addition of 1 mL of Span 80 as an emulsifier. To this solution, 1 mL of coacervate is added and mixed using a mechanical stirrer at speeds higher than 1,000 rpm for 90 min, resulting in spherical particles of coacervates dispersed inside a water immiscible solvent, for example, a chloroform solution. This resulting mixture is then added to a water miscible solvent, for example, acetone and mixed at 500 rpm for 3 hr to solidify the particles as shown in FIG. 1. The whole of this final solution is centrifuged in separate falcon tubes at 4,400 rpm for 5 min to collect the PGMs at the bottom and the top supernatant solution is discarded. Subsequently, PGMs are first washed twice with chloroform and then twice with acetone prior to cold storage in acetone. Depending on the incorporated cation or the therapeutic agent, PGMs could have different colors. The composition of the PGMs could be manipulated by incorporating other therapeutic cations such as antibacterial $Cu^{2+}$, radioactive Yttrium ($^{90}Y^{3+}$) or diagnostic cations such as radioactive technetium ($^{99}Tc$) during coacervate formation. Also the size distribution can be controlled by factors such as NaPP Dp, mixing speed, thickening agent concentration or organic phase volume.

Step 4—Stabilizing PGMs

PGMs immediately aggregate upon contact with water. If aggregation is not desired then a stabilizing step may be performed. In various embodiments, aggregation can be prevented by keeping the PGMs in a highly concentrated Sr or Ba solution. For example, PGMs with a size smaller than 20 μm are kept in 1 M $BaCl_2$ at a temperature ranging from about 0° C. to about 10° C. for less than 24 hrs. Then the Ba solution is discarded and replaced with fresh water. These PGMs do not aggregate further upon contact with water. In contrast, if water is added to the PGMs without any Ba-incubation they will aggregate immediately. Aggregation can also be prevented by applying a secondary coating on prepared PGM (e.g. polymeric coating) using techniques that are known in the art such as fluidized bed coating.

PGMs provided herein can have any shape. In specific embodiments, these PGMs are substantially spherical in shape. In certain embodiments, the PGMs are uniform shape.

In certain embodiments, the PGMs provided are calibrated to a certain size range. Such calibration can be achieved using method known in the art, such as by one or more rounds of sieving using an appropriately sized mesh sieve. In certain embodiments, the PGMs provided herein have a diameter from about 0.1 μm to 2000 μm, such as from about 0.1 μm to 1200 μm, from 1 μm to 500 μm, from about 10 μm to about 120 μm, from about 20 μm to about 300 μm, from about 100 μm to about 500 μm, from about 300 μm to about 700 μm, from about 500 μm to about 900 μm, or from about 700 μm to about 1200 μm and all ranges therebetween those exemplified herein. In some exemplary applications, the PGMs of the present invention, for use in uterine artery embolization size can range from about 350 μm to about 500 μm or from about 500 μm to about 700 μm are preferred. For Transarterial chemoembolization PGMs can range in size from about 70 μm to about 150 μm, or from about 100 μm to about 300 μm, or from about 300 μm to about 500 μm or from about 500 μm to about 700 μm are preferred. For periodontitis applications, the size of the PGMs can range from about 0.1 μm to 1000 μm, preferably from about 30 μm to about 120 μm. These diameters can permit the PGMs to be delivered to target blood vessels, tissues or organs in vivo via catheter, needle (e.g., a 18 gauge or smaller needle), tubing, or the like by various pathways including vascular, intraductal, transesophogeal, subcutaneous, subdermal, submucosal, transbronchial, or interstitial. In certain embodiments, the PGMs can be eliminated through macrophages or other elements of the immune system or the lymphatic system.

In certain embodiments, the PGMs are uniform in size. In certain embodiments, the PGMs are uniform in size, wherein the difference in diameter between individual PGMs is from about 0 μm to about 100 μm, from about 0.01 μm to about 50 μm, or from about 0.1 μm to about 25 μm, such as 100 μm or less, about 50 μm or less, about 25 μm or less, about 10 μm or less or about 5 μm or less.

Phosphate Glass Particles

In some embodiments, the present invention provides PGMs containing a polyphosphate and cation coascervate, wherein the polyphosphate coacervate has a Mz/P mole ratio equal to (1/z), where z represents the valency of the cation. The phosphate polymer in the PGMs have a degree of polymerization (Dp) ranging from about 3 to about 20,000.

In various embodiments, the PGMs of the present invention have a therapeutic agent contained within the PGM, uniformly distributed and is able to be released in a controlled manner. Furthermore, the PGMs of the present invention can have a therapeutic agent loaded within the PGM that is active and stable when released from the PGM under conditions that promote release of the therapeutic agent from the PGMs. In some embodiments, the therapeutic agent can include: a drug, a medicament, a pharmaceutical agent including a disinfecting agent, e.g. an antimicrobial agent, an anti-inflammatory agent, a vaccine, an anti-tumor agent, a drug, radioactive or non-radioactive contrasting agents, or a natural product such as ions, (e.g. monovalent, divalent or trivalent cations or anions, e.g. Cu or Ag ions) or a biologically active agent, for example, a biological growth factor, a peptide, a polypeptide, a protein, a lipid, or a nucleic acid.

Advantageously, the PGMs of the present invention are made from a polyphosphate/cation coascervate that enables incorporation of the therapeutic agent in a non-destructive manner that preserves the activity of the therapeutic agent when administered and released from the PGMs. In some embodiments, the activity of the therapeutic agent when released from the PGMs is at least 50%, or at least 60%, or at least 70%, or at least 80%, or at least 90%, or at least 95%, or at least 99% when compared to the same amount of therapeutic agent not encapsulated into PGMs of the present invention, when tested either in vitro, or in vivo. One of the unexpected properties of the PGMs described herein, is that heat labile therapeutic agents, for example, biologically active agents, such as peptides, polypeptides, proteins, lipids, glycolipids, carbohydrates, and nucleic acids, and certain drugs or medicaments, can be incorporated with the polyphosphate coacervate during synthesis and made into PGMs without exposure to high heat (>50-100° C.) as required in the synthesis of other PGMs. Accordingly, the therapeutic agent retains substantially the majority of its activity when compared to the therapeutic agent not so incorporated into the PGMs or the starting material.

In certain embodiments, the PGMs are uniform in size, wherein the difference in diameter between individual PGMs is from about 0 μm to about 100 μm, from about 0.01 μm to about 50 μm, or from about 0.1 μm to about 25 μm, such as 100 μm or less, about 50 μm or less, about 25 μm or less, about 10 μm or less or about 5 μm or less.

B. Implantable Spherical Phosphate Glass Particles

The PGMs and aggregates of PGMs discussed above can be used as carriers of a therapeutic agent, for example, a biological growth factor, a pharmaceutical agent including a disinfecting agent, e.g. an antimicrobial agent, an anti-inflammatory agent, a vaccine, an anti-tumor agent, a drug, radioactive or non-radioactive contrasting agents, or a natural product such as ions, (e.g. monovalent, divalent or trivalent cations or anions, e.g. Cu or Ag ions) or a biologically active agent, for example, a peptide, a polypeptide, a protein, a lipid, or a nucleic acid. The PGMs of the present invention can be made to have different sizes and therefore have different loading capacities of therapeutic agents. In various embodiments, PGMs of the present invention degrade naturally at the site of implantation and release the contents in a controlled manner. Also, these PGMs and compositions containing such PGMs can be used to culture tissues which may be subsequently implanted to augment tissue defects, such as for augmenting tissue defects in bone and cartilage. In one embodiment, periodontal defects can be treated with PGMs loaded with one or more therapeutic agents, which may in combination speed the repair and improve the resolution of the defect. In one embodiment, PGMs containing either or both an antimicrobial agent and a morphogentic therapeutic agent, for example a BMP can be added to a periodontal defect to treat periodontitis. In other illustrative and non-limiting examples, PGMs can be loaded with antibiotics, and implanted into osseous defects for treatment of osteomyelitis. In another embodiment, PGMs of the present invention loaded with $^{90}$yttrium can be used for radioembolization and chemotherapeutic loaded PGMs, for example, doxorubicin loaded PGMs can be used for chemoembolization and treatment of various solid tumors, for example, hepatocellular carcinoma.

In some embodiments, the PGMs of the present disclosure can be loaded with a chemotherapeutic agent. In various embodiments, chemotherapeutic agent is an agent that is toxic to, arrests the growth of, or prevents the metastasis of a tumor or cancer cell. The chemotherapeutic agent can be a small molecule, for example an organic molecule having a molecular weight less than 1,000 Da. or less than 750 Da. or less than 500 Da. In other embodiments, the chemotherapeutic agent is a biologically active agent, for example, a protein or polypeptide, a nucleic acid or combinations thereof, for example, an antibody or fragment thereof or an antibody or other protein conjugated to a toxic agent, for example, ado-trastuzumab emtansine (T-DM1 or KADCYLA®).

In some embodiments, the chemotherapeutic can include one or more anti-neoplastic agents, for example, Trastuzumab (e.g. anti-HER2), Ranibizumab (e.g. anti-VEGF-A), Bevacizumab (trade name Avastin, e.g. anti-VEGF, Panitumumab (e.g. anti-EGFR), Cetuximab (e.g. anti-EGFR), Rituxan (anti-CD20) and antibodies directed to c-MET, a cytostatic agent, cisplatin, doxorubicin, taxotere, taxol, etoposide, irinotecan, camptostar, topotecan, paclitaxel, docetaxel, epothilones, tamoxifen, 5-fluorouracil, methoxtrexate, temozolomide, cyclophosphamide, SCH 66336, R115777, L778,123, BMS 214662, Iressa, Tarceva, antibodies to EGFR, GLEEVEC™, intron, ara-C, adriamycin, cytoxan, gemcitabine, Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, ELOXATIN™, Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17 alpha-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, Bexxar, Velcade, Zevalin, Trisenox, Xeloda, Vinorelbine, Porfimer, Erbitux, Liposomal, Thiotepa, Altretamine, Melphalan, Lerozole, Fulvestrant, Exemestane, Fulvestrant, Ifosfomide, Rituximab, C225, Campath, Clofarabine, cladribine, aphidicolon, rituxan, sunitinib, dasatinib, tezacitabine, Sml1, fludarabine, pentostatin, triapine, didox, trimidox, amidox, 3-AP, MDL-101,731, bendamustine (Treanda), ofatumumab, and GS-1101 (also known as CAL-101), a PARP inhibitor, for example, Olaparib, Niraparib (MK-4827), Iniparib (BSI 201), Talazoparib (BMN-673), Veliparib (ABT-888), Rucaparib (AG014699, PF-01367338), CEP 9722, E7016 (Eisai), BGB-290, 3-aminobenzamide, and combinations of all of the aforementioned chemotherapeutic agents.

Other examplary chemotherapeutics include proteosome inhibitors (e.g., bortezomib), thalidomide, revlimid, and DNA-damaging agents such as melphalan, doxorubicin, cyclophosphamide, vincristine, etoposide, carmustine, and the like, steroids including coriticosteroids such as dexamethasone or prednisone, Bcr-Abl inhibitors including the compounds, and pharmaceutically acceptable salts thereof, of the genera and species disclosed in U.S. Pat. No. 5,521,184, WO 04/005281, and U.S. Ser. No. 60/578,491, Flt-3 inhibitors including compounds, and their pharmaceutically acceptable salts, as disclosed in WO 03/037347, WO 03/099771, and WO 04/046120, RAF inhibitors including compounds, and their pharmaceutically acceptable salts, as disclosed in WO 00/09495 and WO 05/028444, FAK inhibitors including compounds, and their pharmaceutically acceptable salts, as disclosed in WO 04/080980, WO 04/056786, WO 03/024967, WO 01/064655, WO 00/053595, and WO 01/014402, mTOR inhibitors include compounds, and their pharmaceutically acceptable salts, as disclosed in WO 2011/025889. All of the above referenced patent disclosures are incorporated herein in their entireties.

In some embodiments, PGMs can be imbedded in additional substrates or tissues provide a central cavity as a reservoir for therapeutic agents. The PGMs provide compressive strength due to their geometry as a basic sphere in distributing mechanical stress within their walls. In addition, the PGMs can be replaced by tissue in-growth as the material within the wall resorbs thereby serving as an osteoconductive substrate for the growth of stem cells, such as mesenchymal stem cells, osteoblasts. A typical application for PGMs and bonded aggregates of PGMs is the repair and augmentation of bony defects, for example, in dental and orthopedic applications. Also, PGMs of smaller sizes can be used to augment soft tissue, e.g., cartilage defects.

The degree of resorbability may be adjusted by changing the composition of the coacervate (for instance substituting some of the $Ca^{2+}$ with $Sr^{2+}$ or $Ba^{2+}$, or using longer polyphosphate chains, or applying a secondary coating (e.g. polymeric coating) on the PGMs).

Oral Tissue Applications

In some embodiments, the PGMs of the present disclosure may be used to treat oral defects such as periodontal defects, oral-maxillofacial defects and bone replacement for plastic surgical or oncological applications. In one example the subject may present with gingivitis, resorption of alveolar bone and eventual tooth loss stemming from progressive loss of collagen attachment of the tooth to alveolar bone. Other lesions of mucosal or related oral tissue are possible. In one embodiment, the disease or condition is a disease or condition of oral tissue. Chronic periodontitis is a particularly important example. Others include diseases and conditions characterized by damage to oral mucosa as in Scarlet Fever, Aphthous Stomatitis, Pyogenic Granuloma, Diphtheria, Tuberculosis, Syphilis, Actinomycosis, Candidiasis, Herpetic Stomatitis.

It will be understood that the disease or condition may be a disease or condition of a tissue other than the oral tissue such as an organ or system, for example, the skeletal-musculo system, or the cardiovascular system.

The invention is applicable to treatment of oral and osseous defects, such as periodontitis, osteonecrosis, osteoporosis, osteomyelitis, trauma; repair, augmentation or restoration associated with cleft lip/palate surgery and the like, where the first or one of the important objectives is to prevent or treat a microbial infection, prior, during or after a medical procedure. In one illustrative example, a range of microbial pathogens, especially those that infect the tissues of the oral cavity can be treated using the PGMs of the present invention. In one embodiment, the pathogen is selected from the group consisting of bacteria, virus and fungi. In exemplary embodiment, PGMs loaded with minocycline are prepared in accordance with the methods disclosed herein. Minocycline loaded PGMs can be prepared and used to treat a patient with periodontitis. Oral bacteria that can be controlled or inhibited for periodontal and other dental applications can include: *Porphyromonas gingivalis, Treponema denticola, Tannerella forsythia.*

Exemplary oral pathogenic organisms that can be inhibited using the antimicrobial agent loaded PGMs can include *Streptococci* Sp. including: *S. salivarius, S. mutans, S. sanguis, S. pneumonia, S. pyogenes, S. mitis Neisseria meningitides, Lactobacilli plantarum, Proteus, Bacteroides, Staphylococcus epidermidis, Staphylococcus aureus, Pseudomonas aeruginosa, Clostridium perfringens, Clostridium tetani, Corynebacteria, Enterococci faecalis, Veillonella, Treponema denticola, Porphyromonas gingivalis, Tanneralla forsythia, Aggregatibacter actinomycetemcomitans, Actinomycetes Spirochetes, Mycoplasmas, Fungi, Candida albicans, Candida khmerensis, Candida metapsilosis, Candida parapsilosis, Candida tropicalis, Cladosporium cladosporioides, Cladosporium sphaerospermum, Cladosporium herbarum, Cladosporium tenuissimum, Aureobasidium pullulans, Saccharomycetales, Fusarium culmorum, Fusarium oxysporum, Fusarium poae, Aspergillus amstelodami, Aspergillus caesiellus, Aspergillus flavus, Aspergillus oryzae, Aspergillus penicillioides, Aspergillus ruber, Xylariales, Glomus fulvum, Glomus mosseae, Leptosphaeriaceae, Ascomycete, Basidiomycete, Ophiostoma floccosum, Ophiostoma pulvinisporum, Ectomycorrhiza, Penicillium brevicompactum, Penicillium glabrum, Penicillium spinulosum, Endophytic fungi, Glomeromycete., Alter-*

*naria tenuissima, Alternaria triticina, Cryptococcus cellulolyticus, Cryptococcus diffluens, Phoma foveata, Phoma plurivora Saccharomyces bayanus, Saccharomyces cerevisiae, Saccharomyces ellipsoideus, Schizosaccharomyces japonicas, Schizosaccharomyces pombe, Zygosaccharomyces pseudorouxii, Zygosaccharomyces rouxii, Protozoa, Entamoeba, Gingivalis, Trichomonas, Tenax,* and *Leishmania brasiliensis.*

Without being bound by any theory or mode of action, it is believed that application of an antimicrobial agent contained with PGMs as defined herein, for example in a periodontal gel formulation, at the time of mechanical debridement and cleaning of the infected periodontal site, helps to prevent subsequent re-emergence of the periodontal pathogens and prevention of disease progression.

In this context, the following may be antimicrobial agents: an antibiotic, an immunosuppressant and an antiseptic. In certain embodiments the agent may be an anti-inflammatory agent. Anti-inflammatory agents include Nonsteroidal Anti-inflammatory Drugs (NSAIDs). Examples of NSAIDs include compounds than inhibit a cyclooxygenase. Specific examples of NSAIDs include aspirin, ibuprofen and naproxen.

In one particularly preferred embodiment, the antimicrobial agent is an antibiotic. Examples include antibiotics selected from the group consisting of macrolides, tetracyclines, penicillins, fumarate reductase inhibitors and antimicrobial peptides.

In some embodiments, the antimicrobial agent can include the following agents: (i) cephalosporins such as cephalexin, cefoxytin and cephalothin; (ii) penicillins such as amoxycillin, amoxycillin with clavulanic acid, ampicillin, bacampicillin, benzathine penicillin, benzylpenicillin, carbenicillin, cloxacillin, methicillin, phenethicillin, phenoxymethylpenicillin, flucloxacillin, mezlocillin, piperacillin, ticarcillin and azlocillin; (iii) tetracyclines such as minocycline, chlortetracycline, tetracycline, demeclocycline, doxycycline, methacycline and oxytetracycline and other tetracycline-type antibiotics; (iv) minoglycosides such as amikacin, gentamicin, kanamycin, neomycin, netilmicin and tobramycin. Antifungals such as amorolfine, isoconazole, clotrimazole, econazole, miconazole, nystatin, terbinafine, bifonazole, amphotericin, griseofulvin, ketoconazole, fluconazole and flucytosine, salicylic acid, fezatione, ticlatone, tolnaftate, triacetin, zinc, pyrithione and sodium pyrithione; (v) Quinolones such as nalidixic acid, cinoxacin, ciprofloxacin, enoxacin and norfloxacin. Sulphonamides such as phthalylsulphthiazole, sulfadoxine, sulphadiazine, sulphamethizole and sulphamethoxazole; (vi) Sulphones such as dapsone; and (vii) Other miscellaneous antibiotics such as chloramphenicol, clindamycin, erythromycin, erythromycin ethyl carbonate, erythromycin estolate, erythromycin glucepate, erythromycin ethylsuccinate, erythromycin lactobionate, roxithromycin, lincomycin, natamycin, nitrofurantoin, spectinomycin, vancomycin, aztreonam, colistin IV, metronidazole, tinidazole, fusidic acid and trimethoprim; 2-thiopyridine N-oxide; halogen compounds, particularly iodine and iodine compounds such as iodine-PVP complex and diiodohydroxyquin; hexachlorophene; chlorhexidine; chloroamine compounds; benzoylperoxide (z) Anti-tuberculosis drugs such as ethambutol, isoniazid, pyrazinamide, rifampicin and clofazimine. Antimalarials such as primaquine, pyrimethamine, chloroquine, hydroxychloroquine, quinine, mefloquine and halofantrine. (aa) Antiviral agents such as acyclovir and acyclovir prodrugs, famciclovir, zidovudine, didanosine, stavudine, lamivudine, zalcitabine, saquinavir, indinavir, ritonavir, n-docosanol, tromantadine and idoxuridine. Anthelmintics such as mebendazole, thiabendazole, niclosamide, praziquantel, pyrantel embonate and diethylcarbamazine.

The antibiotic may be directly cytotoxic to the microbial pathogen. In other embodiments, the antibiotic is indirectly cytotoxic, for example, the antibiotic may be an inhibitor of microbial biofilm production or some other metabolism.

Thus, the PGMs provided herein have a wide variety of applications. For example, the PGMs provided herein can also be used for embolization, tissue engineering, tissue guided regeneration, in vivo stem cell harvesting, culturing, or differentiation, hemostasis, delivery and suspension of therapeutic materials in targeted human or animal tissues and/or other applications.

Any of the various PGMs provided herein, or prepared by the various methods provided herein, can be used in any the various embolization and disease management and treatment embodiments provided herein. In one embodiment, provided is a method of embolization in a subject, comprising administering to the subject, PGMs provided herein. In another embodiment, provided herein is a method of managing or treating an angiogenesis-dependent disease in a subject, comprising administering to the subject PGMs provided herein. In one embodiment, the angiogenesis-dependent disease is arteriovenous malformation, uterine fibroid, or benign prostatic hyperplasia. In an embodiment, the angiogenesis-dependent disease is a cancer or tumor, such as a liver or prostate cancer or tumor.

Embolization

There are a number of clinical situations (e.g., bleeding, tumor development) where it is desirable to reduce or abolish the blood supply to an organ or region. As described in greater detail below, this can be accomplished by injecting the PGMs or compositions containing PGMs into a desired blood vessel through a selectively positioned needle or catheter, or under the guidance of an x-ray camera (e.g., a fluoroscope). The PGMs or compositions containing PGMs travel via the blood stream until it becomes wedged in the vasculature, thereby physically (or chemically) occluding the blood vessel. The reduced or abolished blood flow to the selected area results in infarction (cell death due to an inadequate supply of oxygen and nutrients) or reduced blood loss from a damaged vessel.

Thus, in certain embodiments, provided herein is a method of embolization in a subject or patient, comprising administering to the subject a PGM or a composition comprising the PGMs. In one embodiment, provided are methods for embolizing a blood vessel, comprising administering to the vessel of a subject or patient a therapeutically effective amount of the PGMs, such that the blood vessel is effectively occluded. In some embodiments, embolization can be accomplished in order to treat or prevent conditions of excessive bleeding. Embolization therapy utilizing PGMs or compositions containing PGMs provided herein can also be applied to a variety of other clinical situations where it is desired to occlude blood vessels, for example, for acute bleeding, vascular abnormalities, central nervous system disorders, and hypersplenism.

In the case of vascular malformations, such as AVM or arteriovenous fistulas, vascular occlusion enables the blood flow to the tissues to be normalized, aids in surgery, and limits the risk of hemorrhage. In hemorrhagic processes, vascular occlusion produces a reduction of flow, which promotes cicatrization of the arterial opening(s).

Embolization can be used in the treatment of uterine fibroids, postpartum and/or post-caesarian bleeding, post-surgical vaginal bleeding, the prevention and/or treatment of hemorrhage from ectopic pregnancy, prophylactically prior to myomectomy and in obstetrical patients at high risk for bleeding, such as those patients with placenta previa, placenta accreta, and twin fetal death. Embolization can also be used to stop uncontrolled bleeding, or to slow bleeding prior or during surgery, and for sealing endoleaks into aneurysm sacs.

Any of the various diseases or disorders provided herein, or a symptom thereof, can be managed, treated or prevented according the methods provided herein. Furthermore, depending on the pathological conditions treated, embolization can be carried out for temporary as well as permanent objectives.

Embolization can also be used in combination with other clinical procedures, such as angiography. For example, a radiopaque contrast agent can be injected to the area to be embolized through, e.g., a catheter inserted percutaneously or by surgery into an artery or vein as an x-ray is taken. The blood vessel can then be embolized by refluxing PGMs provided herein through the catheter, until flow is observed to cease. Occlusion can be confirmed by repeating the angiogram.

The PGMs provided herein can be administered to (or otherwise contacted with) a blood vessel, a tissue or organ (e.g., heart, kidney, spinal cord, uterus, liver or pancreas) by means known in the art. In certain embodiments, the PGMs are administered (e.g., by injection) to a tissue or organ that has more than one blood supply, for example the liver, lung, spine, spinal cord, uterus or pancreas. In certain embodiments, the PGMs are administered to the heart, lung, nervous system, brain, lung, liver, uterus or pancreas of the patient. In some embodiments, the PGMs are administered to one or more blood vessels, veins or arteries comprised within the tissue or organ. In certain embodiments, the PGMs provided herein are used to counter ischemia in the target area, e.g., the area of administration or injection, such as in or near a tissue or organ. In some embodiments of the methods provided herein, the PGMs are administered to a patient by intraluminal administration or injection. In other embodiments of the methods provided herein, the PGMs are administered to a patient by intravascular administration or injection.

The PGMs can be delivered systemically or locally to the desired blood vessel, tissue or organ. In some embodiments, the PGMs are administered to a blood vessel, tissue or organ before, during or after a surgery. In other embodiments, the PGMs are delivered to a blood vessel, tissue or organ using non-surgical methods, for example, either locally by direct injection into the target area, to a remote site and allowed to passively circulate to the target site, or to a remote site and actively directed to the target site. Such non-surgical delivery methods include, for example, infusion or intravascular (e.g., intravenous or intraarterial), intramuscular, intraperitoneal, intrathecal, intradermal or subcutaneous administration. In certain embodiments, angiography (e.g., selective angiography or superselective angiography) is used in conjunction with embolization to assess the blood supply to the tissue or organ. In such embodiments, an angiogram can be taken prior to, during, or after embolization.

Diseases or disorders provided herein can be treated or otherwise managed by administering to the patient (e.g., a patient in need thereof) a therapeutically effective amount of the PGMs or a composition provided herein to provide safe and effective embolization.

In certain embodiments, administration is carried out by injection. In certain embodiments, the PGMs are administered by a catheter. In other embodiments, the PGMs are injected using a needle attached to a syringe. In some embodiments, administration is into a blood vessel. In other embodiments, administration is directly to the site of action, for example into a tooth or part of a tooth, into a bone defect, into a tumor mass, or into a cell, organ or tissue requiring such treatment or management. In some embodiments, the PGMs are administered in combination with a drug solution or other therapy, wherein the drug solution or other therapy is administered prior, simultaneously or after the administration of the PGMs.

It should be understood that the patients suitable for embolization with the PGMs provided herein include humans and animals, including male and female infants, children, and adults, including the elderly. In a specific embodiment, the patient is at risk for, or currently afflicted with, hepatocellular diseases, such as hepatitis or a liver cancer or tumor.

PGMs and compositions provided herein can also be in combination with drugs or other therapies. For example, the PGMs and compositions can be used to treat or otherwise manage tumors or cancers (e.g., prostate or liver cancer), inflammatory diseases or other diseases associated with inflammation, or a symptom thereof. In other embodiments, the PGMs and compositions provided herein can be used to treat or otherwise manage uterine fibroids, or a symptom thereof. In other embodiments, the PGMs and compositions provided herein can be used to treat or otherwise manage a vascular malformation, such as an AVM, or a symptom thereof. In yet other embodiments, the PGMs and compositions provided herein can be used to treat or otherwise manage a prostate disease, such as a benign prostate hyperplasia, or a symptom thereof.

In certain embodiments, a drug or other therapy is administered concurrently to the subject in combination with the PGMs provided herein. In some embodiments, a drug or other therapy is administered to the subject prior to administration of PGMs. In certain embodiments, a drug or other therapy is administered from about 1 minute to about 60 minutes prior to administration of PGMs. In some embodiments, a drug or other therapy is administered to the subject within about 1 minute, about 5 minutes, about 10 minutes, about 15 minutes, about 20 minutes, about 30 minutes, about 45 minutes or about 1 hour, about 2 hours, about 4 hours, about 6 hours, about 10 hours, about 12 hours, about 18 hours, about 20 hours or about 24 hours of administration of PGMs. In yet other embodiments, a drug or other therapy is administered concurrently with PGMs. In certain embodiments, PGMs are administered to the subject prior to administration of a drug or other therapy. In certain embodiments, PGMs are administered between about 1 minute and about 60 minutes prior to administration of a drug or other therapy. In some embodiments, PGMs are administered to the subject within about 1 minute, about 5 minutes, about 10 minutes, about 15 minutes, about 20 minutes, about 30 minutes, about 45 minutes or about 1 hour, about 2 hours, about 4 hours, about 6 hours, about 10 hours, about 12 hours, about 18 hours, about 20 hours or about 24 hours of administration of a drug or other therapy.

Angiogenesis-Dependent Diseases

Angiogenesis-dependent diseases (i.e., those diseases which require or induce vascular growth) represent a significant portion of all diseases for which medical treatment is sought. Such diseases include, for example, cancers or tumors (e.g., liver cancers or tumors, or prostate cancer or tumors) and non-tumorigenic angiogenesis-dependent diseases.

In certain embodiments, provided herein are PGMs, compositions and methods suitable for treating or otherwise managing angiogenesis-dependent diseases, including tumors or other cancers, non-tumorigenic angiogenesis-dependent diseases, or pain, such as pain related to the presence of a tumor or other cancer, or a symptom thereof. In one embodiment, methods are provided for managing or treating an angiogenesis-dependent disease in a subject, comprising administering to the subject a microsphere (PGMs) or a composition comprising the microsphere(s). In specific embodiments, methods are provided for managing or treating an angiogenesis-dependent diseases in a subject comprising, for example, administering to the subject PGMs or a composition comprising the PGMs. In certain embodiment, the PGMs are loaded with a therapeutic agent that inhibits or otherwise diminishes angiogenesis, particularly, angiogenesis involved in tumor growth.

In addition to cancer, numerous other non-tumorigenic angiogenesis-dependent diseases which are characterized by the abnormal growth of blood vessels can also be treated, either via down-regulation or up-regulation, or otherwise managed with the PGMs or compositions provided herein. Representative examples of such non-tumorigenic angiogenesis-dependent diseases include, without limitation, hypertrophic scars and keloids, proliferative diabetic retinopathy, rheumatoid arthritis, arteriovenous malformation (AVM), lymphangitic malformations, venous malformations, atherosclerotic plaques, delayed wound healing, hemophilic joints, nonunion fractures Klippel Trenaunay Syndrome, Parkes Weber Syndrome, Osler-Weber-Rendu Syndrome, Blue Rubber Bleb Syndrome, cutaneous and subcutaneous nevi, hemangiomas, leiomyomata, adenomas, hamartomas, psoriasis, pyogenic granuloma, scleroderma, tracoma, menorrhagia, vascular adhesions, benign prostatic hyperplasia (BPH) and uterine fibroids.

Cancers or Tumors

In specific embodiments, methods are provided for managing or treating a cancer or tumor (e.g., a hypervascularized cancer or tumor) in a subject comprising, for example, administering to the subject a PGMs or a composition comprising the PGMs containing either a chemotherapeutic agent or an anti-angiogenic agent or both. Such cancers include, without limitation (both anatomically and by primary neoplastic site), liver, ovarian, breast, kidney, lung, pancreatic, thyroid, prostate, uterine, skin cancer, head and neck tumors, breast tumors, brain, bone, soft tissues (such as sarcoma, lipoma, malignany fibrous histiocytoma), blood (such as lymphoma), Kaposi's sarcoma, and superficial forms of bladder cancer. In certain embodiments, the method of treatment or management can be the result of localized (or systemic) drug delivery in combination with embolic effects of the PGMs (e.g., TACE).

Other diseases, and symptoms thereof, contemplated for management and treatment with the compositions and methods provided herein include, for example, without limitation, tumors associated with the liver, kidney, acute lymphoblastic leukemia, acute myeloid leukemia, Ewing's sarcoma, gestational trophoblastic carcinoma, Hodgkin's disease, non-Hodgkin's lymphoma, Burkitt's lymphoma diffuse large cell lymphoma, follicular mixed lymphoma, lymphoblastic lymphoma, rhabdomyosarcoma, testicular carcinoma, wilms's tumor, anal carcinoma, bladder carcinoma, breast carcinoma, chronic lymphocytic leukemia, chronic myelogenous leukemia, hairy cell leukemia, head and neck carcinoma, meningioma, neuro fibrosoma, angio fibrosoma, lung (small cell) carcinoma, multiple myeloma, Non-Hodgkin's lymphoma, follicular lymphoma, ovarian carcinoma, brain tumors (astrocytoma), cervical carcinoma, colorectal carcinoma, hepatocellular carcinoma, human large hepatocellular carcinoma, Kaposi's sarcoma, lung (non-small-cell) carcinoma, melanoma, pancreatic carcinoma, prostate carcinoma, soft tissue sarcoma, breast carcinoma, colorectal carcinoma (stage 11), bone tumors, osteogenic sarcoma, ovarian carcinoma, testicular carcinoma, or combinations thereof.

Embolization therapy using the PGMs or compositions provided herein can be utilized in at least three principal ways to assist in the management of neoplasms: (1) definitive treatment of tumors (usually benign); (2) for preoperative embolization; and (3) for palliative embolization. Briefly, benign tumors can sometimes be successfully treated by embolization therapy alone. Examples of such tumors include simple tumors of vascular origin (e.g., haemangiomas), endocrine tumors such as parathyroid adenomas, and benign bone tumors.

For other tumors, (e.g., renal adenocarcinoma), preoperative embolization can be employed hours or days before surgical resection in order to reduce operative blood loss, shorten the duration of the operation, and reduce the risk of dissemination of viable malignant cells by surgical manipulation of the tumor. Many tumors can be successfully embolized preoperatively, including for example nasopharyngeal tumors, glomus jugular tumors, meningiomas, chemodectomas, and vagal neuromas.

Embolization using the PGMs or compositions can also be utilized as a primary mode of treatment for inoperable malignancies, in order to extend the survival time of patients with advanced disease. Embolization can produce a marked improvement in the quality of life of patients with malignant tumors by alleviating unpleasant symptoms such as bleeding, venous obstruction and tracheal compression. The benefits from palliative tumor embolization, in certain embodiments, can be seen in patients suffering from the humoral effects of malignant endocrine tumors, wherein metastases from carcinoid tumors and other endocrine neoplasms such as insulinomas and glucagonomas can be slow growing, and yet still cause great distress by virtue of the endocrine syndromes which they produce. In certain embodiments, embolization therapy can also be used during surgery to remove a tumor or vascular mass or cancerous organ, or to prevent or ameliorate metastasis.

Chemoembolization is a combination of chemotherapy and embolization or embolotherapy, used typically to treat cancer. Similarly, radioembolization is a combination of radiation therapy and embolization or embolotherapy. In certain embodiments, the PGMs provided herein can be injected to a target area as a standalone therapy or for the purposes of interspersion between terminal therapeutic PGMs to allow for gradual migration of the PGMs into tumor blood supply, while providing continued perfusion/blood flow into targeted tumor. The addition of chemotherapeutics to PGMs can increase the efficacy of the therapy by improving the timing of exposure of therapy with the terminal embolic effect of the administered PGMs.

A wide variety of cancers or tumors may be embolized utilizing a microsphere composition provided herein. Briefly, tumors are typically divided into two classes: benign and malignant. In a benign tumor, the cells can retain their differentiated features and do not divide in a completely uncontrolled manner. In addition, the tumor is localized and non-metastatic. In a malignant tumor, the cells can become undifferentiated, do not respond to the body's growth and hormonal signals, and multiply in an uncontrolled manner; the tumor is invasive and capable of spreading to distant sites (metastasizing). Bother benign and malignant tumors can be embolized, treated, managed, prevented or ameliorated using the PGMs provided herein.

In certain embodiments, also provided herein are methods of managing or treating secondary tumors or metastatic tumors (e.g., secondary hepatic tumors) using the PGMs or compositions provided herein. A secondary tumor, or metastasis, is a tumor which originated elsewhere in the body but has subsequently spread to a distant organ. The common routes for metastasis are direct growth into adjacent structures, spread through the vascular or lymphatic systems, and tracking along tissue planes and body spaces (peritoneal fluid, cerebrospinal fluid, etc.).

In other embodiments of the methods provided herein, embolization therapy may be used during surgery to remove a tumor or vascular mass or cancerous organ. Additionally, therapeutic embolization therapy can be used to treat, manage, prevent or ameliorate metastasis.

In certain embodiments, blood vessels which nourish a tumor are deliberately blocked by injection of an embolic material into the vessel. Notably, in the case of tumors, vascular occlusion methods provided herein can be used to suppress pain, limit blood loss on the surgical intervention to follow embolization, or even bring on a tumoral necrosis and avoid an operation.

Liver Cancers or Tumors

In certain embodiments, liver cancers or tumors can be treated or managed utilizing the methods comprising administering the PGMs or compositions to the subject. Representative examples of benign hepatic tumors include hepatocellular adenoma, cavernous haemangioma, and focal nodular hyperplasia. Other benign tumors, which are more rare and often do not have clinical manifestations, can also be treated. These include bile duct adenomas, bile duct cystadenomas, fibromas, lipomas, leiomyomas, mesotheliomas, teratomas, myxomas, and nodular regenerative hyperplasia.

Malignant hepatic tumors can be subdivided into two categories: primary and secondary. Primary tumors arise directly from the tissue in which they are found. Thus, a primary liver tumor is derived originally from the cells which make up the liver tissue (such as hepatocytes and biliary cells). Representative examples of primary hepatic malignancies include hepatocellularcarcinoma, cholangiocarcinoma, angiosarcoma, cystadenocarcinoma, squamous cell carcinoma, and hepatoblastoma. Hepatic malignancies, or symptoms thereof, can be treated or otherwise managed, for example, using the compositions and methods provided herein.

Arterial embolization can be done, for example, by injecting PGMs through a small tube, or catheter, threaded into the hepatic artery. For example, a catheter can be inserted via the femoral or brachial artery and advanced into the hepatic artery by steering it through the arterial system under fluoroscopic guidance. The catheter can be advanced into the hepatic arterial tree as far as necessary to allow complete blockage of the blood vessels supplying the tumor(s), while sparing as many of the arterial branches supplying normal structures as possible. This can be, for example, a segmental branch of the hepatic artery, but it could be that the entire hepatic artery distal to the origin of the gastroduodenal artery, or even multiple separate arteries, will need to be blocked depending on the extent of tumor and its individual blood supply. Once the desired catheter position is achieved, the artery can be embolized by injecting anti-angiogenic therapeutic compositions (e.g., PGMs provided herein and optionally one or more additional therapies, e.g. chemotherapeutic agents and/or radiation therapy) through the arterial catheter until flow in the artery to be blocked ceases, such as after observation for 5 minutes. Occlusion of the artery can be confirmed by injecting radiopaque contrast through the catheter and demonstrating by fluoroscopy or x-ray film that the vessel which previously filled with contrast no longer does so. The same procedure can be repeated with each feeding artery to be occluded.

The hepatic artery is the main source of blood for most liver tumors, and thus, PGMs can block the flow of blood to the tumor, depriving it of the nutrients and oxygen it needs to survive. In a similar manner, arterial embolization can be accomplished in a variety of other conditions, including for example, without limitation, for acute bleeding, vascular abnormalities, central nervous system disorders, and hypersplenism. In certain embodiments, transarterial chemoembolization (TACE) and transarterial embolization (TAE) can be performed to treat liver cancers or tumors. TACE is a combination therapy of TAE and regional chemotherapy, which refers to an interventional radiology procedure involving gaining percutaneous access to the hepatic artery, usually by puncturing the common femoral artery in the right groin and passing a catheter through the abdominal aorta, through the celiac axis and common hepatic artery, into the proper hepatic artery (which supplies the liver).

Selective arterial obstruction can induce ischemic tumor necrosis while minimizing damage to the liver tissue. The blood supply to the liver tissue is still maintained by dominant blood flow from the portal vein minimizing damage to the liver. In addition, chemotherapeutic agents concomitantly administered remain in a tumor for a longer period at a higher concentration. The embolotherapy interrupts the arterial blood flow to a tumor and prevents washout of the injected chemotherapeutic agents from a tumor.

TACE can derive its beneficial effect in two ways. Since most tumors are supplied by the hepatic artery, arterial embolization interrupts their blood supply and postpones growth until replaced by neovascularity. Further, focused administration of chemotherapy allows a higher dose to the tissue while simultaneously reducing systemic exposure, which is typically the dose limiting factor. This effect is potentiated by the fact that the chemotherapeutic drug is not washed out from the tumor bed after embolization. Thus, the combination of embolotherapy and regional chemotherapy has synergistic, anti-tumor effects with a high objective response rate. Another added benefit is that the use of combination therapy results in lower systemic drug levels and therefore less toxicity.

In certain embodiments, also provided herein are methods of managing or treating secondary hepatic tumors using the PGMs or compositions provided herein. Secondary hepatic tumors are one of the most common causes of death in the cancer patient and are by far and away the most common form of liver tumors. Although virtually any malignancy can metastasize to the liver, tumors which are most likely to spread to the liver include: cancer of the stomach, colon, and pancreas; melanoma; tumors of the lung, oropharynx, and bladder; Hodgkin's and non-Hodgkin's lymphoma; tumors of the breast, ovary, and prostate. Each one of the above-named primary tumors has numerous different tumor types which can be treated by arterial embolization.

Prostate Cancers or Tumors

In certain embodiments, methods are provided for managing or treating prostate cancers or tumors, or a symptom thereof, using PGMs or compositions provided herein.

In some embodiments, the PGMs or compositions are administered to an area surrounding the prostate, such as, the prostatic artery. For example without limitation, the PGMs or compositions can be delivered to a blood vessel that nourishes the prostate cancer.

The administration of PGMs or compositions can be conducted via a syringe, a catheter, a needle and other means for injecting or infusing. The syringe, the catheter, the needle or the like can be inserted into a vein or an artery, for example, the femoral artery or the inferior vesicle artery.

In certain embodiments, a syringe, a catheter, or a needle is advanced into, for example, the ostium of the prostate arteries and, in one embodiment, advanced as far as necessary to allow complete blockage of the blood vessels supplying a prostate cancer, while sparing as many of the arterial branches supplying normal structures as possible.

In some embodiments of the methods provided herein, angiography of the area to be embolized is performed prior to embolization. The blood vessel is then embolized by refluxing an embolic material provided herein through a previously placed catheter, until flow is observed to cease. The catheter can be inserted either percutaneously or by surgery. Occlusion can be confirmed by repeating the angiogram.

Other cancers and/or tumors in which vascular embolization may be useful include oral cancers—e.g. oral squamous cell carcinoma.

Arteriovenous Malformation

In further specific embodiments, methods are provided for managing or treating arteriovenous malformation or a symptom thereof in a subject comprising, for example, administering to the subject PGMs or a composition comprising the PGMs to occlude arteries or veins to correct the arteriovenous malformation. In one embodiment, the arteriovenous malformation can be treated by inserting a catheter via the femoral or brachial artery, and advancing it into the feeding artery under fluoroscopic guidance. The catheter can be advanced as far as necessary to allow complete blockage of the blood vessels supplying the vascular malformation, while sparing as many of the arterial branches supplying normal structures as possible (ideally this will be a single artery, but most often multiple separate arteries may need to be occluded, depending on the extent of the vascular malformation and its individual blood supply). Once the desired catheter position is achieved, each artery can be embolized utilizing the PGMs or compositions provided herein.

Uterine Fibroids

In further specific embodiments, methods are provided for managing or treating uterine fibroids or a symptom thereof, for example, by using uterine fibroid embolization (UFE) or uterine artery embolization (UAE). The cause of uterine fibroids is unknown. However, they commonly cause heavy menstrual bleeding, pain in the pelvic region, and pressure on the bladder or bowel.

In certain embodiments, embolization (such as UFE) using the PGMs and compositions provided herein can be accomplished in order to treat conditions of excessive bleeding, including excessive bleeding associated with uterine fibroids. For example, menorrhagia (excessive bleeding with menstruation) can be readily treated by embolization of uterine arteries (e.g., branches of the internal iliac arteries bilaterally). In certain embodiments, the compositions and methods provided herein are used to manage or treat symptoms of uterine fibroids, such as heavy menstrual bleeding, pelvic pain or pressure and/or urinary dysfunction.

In some embodiments, a catheter may be inserted via the femoral or brachial artery, and advanced into each uterine artery by steering it through the arterial system under the guidance of an x-ray camera (e.g., a fluoroscope). In certain embodiments, the catheter can be advanced as far as necessary to allow complete blockage of the blood vessels to the uterus, while sparing as many arterial branches that arise from the uterine artery and supply normal structures as possible. In certain embodiments, a single uterine artery on each side may be embolized, but occasionally multiple separate arteries may need to be blocked depending on the individual blood supply. Once the desired catheter position is achieved, each artery can be embolized by administration of the PGMs and compositions as described herein. The administered PGMs block the arteries that provide blood flow, causing the fibroids to shrink, and reliving the symptoms of women with fibroids. In certain embodiments, UAE can also be used to stop severe pelvic bleeding caused, for example, by trauma, malignant gynecological tumors or hemorrhage after childbirth.

Benign Prostatic Hyperplasia

In further specific embodiments, methods are provided for managing or treating benign prostatic hyperplasia (BPH) or a symptom thereof. The most frequent obstructive urinary symptoms are hesitancy, decreased urinary stream, intermittency, sensation of incomplete emptying, nocturia, frequency and urgency.

In certain embodiments, the management or treatment of BPH can be accomplished by embolization such as prostatic artery embolization (PAE) or transcatheter arterial embolization (TAE) using the PGMs and compositions provided herein.

In some embodiments, a catheter (e.g., a microcatheter) can be inserted into the right and/or left inferior vesicle arteries under the guidance of an x-ray camera (e.g., a fluoroscope). In certain embodiments, the catheter can be advanced as far as necessary to allow complete blockage of the blood vessels to the prostate, while sparing as many arterial branches that arise from the prostate artery and supply normal structures as possible.

In certain embodiments, angiography (e.g., initial pelvic angiography or selective digital subtraction angiography) can be used in conjunction with embolization to evaluate the iliac vessels and prostate arteries during the arterial and late phases, or to assess the blood supply to the prostate. Once the desired catheter position is achieved, each artery can be embolized by administration of the PGMs and compositions as described above. The administered PGMs can block the arteries that provide blood flow, reducing the prostate size, and reliving the symptoms of BPH. In certain embodiments, embolization can also be used to control massive hemorrhage after prostatectomy or prostate biopsy.

Diagnostic Imaging

As discussed above, the PGMs provide herein may be used in connection with diagnostic imaging, therapeutic imaging and therapeutic drug delivery, including, for example, ultrasound (US), magnetic resonance imaging (I), nuclear magnetic resonance (NMR), computed tomography (CT), electron spin resonance (ESR), nuclear medical imaging, optical imaging, elastography, drug delivery with ultrasound, radiofrequency (RF) and microwave laser.

In certain embodiments, the PGMs provided herein are fluoroscopically visible. That is, in some embodiments, the PGMs are loaded with, or otherwise contain one or more suitable contrast agents, such as an ionic or non-ionic contrast agent. PGMs can also become intrinsically radiopaque through substituting calcium with elements having high atomic number such as barium.

In some embodiments, the PGMs provided herein comprise a non-ionic contrast agent. The contrast agent can be loaded on the microsphere, associated with the microsphere, absorbed by, adsorbed by or otherwise contained in or on the microsphere. Alternatively, the contrast agent is a carrier solution for the microsphere. In specific embodiments, the contrast agent, such as a non-ionic contrast agent, is loaded within the microsphere (e.g., by mixing of otherwise contacting the contrast agent with the PGMs). In other embodiments, the PGMs do not comprise a contrast agent, such as a non-ionic contrast agent.

The non-ionic contrast agents can be an X-ray, CT, MRI contrast agent, or a combination thereof. The contrast agent can be paramagnetic or superparamagnetic. In some embodiments, the contrast agent is an X-ray contrast agent (also referred to as fluoroscopic agent or radioopaque) or a CT contrast agent. In certain embodiments, the agent within the PGM contains iodine. The non-ionic contrast agents can be monomeric, dimeric, or polymeric.

Examples of non-ionic contrast agents include, without limitation, metrizamide, iopamidol (Isovue™ or Iopamiron™), iodixanol (Visipaque™), iohexyl (Omnipaque™) iopromide (Ultravist™), iobtiridol, iomeprol, iopentol, iopamiron, ioxilan, iotrolan, gadodiamide, gadoteridol, iotrol, ioversol (Optiray™) or combinations thereof. In certain embodiments, the contrast agent is iopamidol. In specific embodiments, the non-ionic contrast agent contained within the PGMs is iodixanol, iohexyl, iopromide, or ioversol. In another embodiment, the non-ionic contrast agent is gadodiamide or gadoteridol.

Further examples of suitable contrast agents for use in combination with the present stabilizing materials include stable free radicals, such as, stable nitroxides, as well as compounds comprising transition, lanthanide and actinide elements, which may, if desired, be in the form of a salt or may be covalently or non-covalently bound to complexing agents, including lipophilic derivatives thereof, or to proteinaceous macromolecules. The transition, lanthanide and actinide elements can include, for example, Gd(III), Mn(II), Cu(II), Cr(III), Fe(II), Fe(III), Co(II), Er(II), Ni(II), Eu(III) and Dy(III). In some embodiments, the elements are Gd(III), Mn(II), Cu(II), Fe(II), Fe(III), Eu(III) and Dy(III). The foregoing elements may be in the form of a salt, including inorganic salts, such as a manganese salt, for example, manganese chloride, manganese carbonate, manganese acetate, and organic salts, such as manganese gluconate and manganese hydroxylapatite. Other exemplary salts include salts of iron, such as iron sulfides, and ferric salts, such as ferric chloride.

The above elements may also be bound, for example, through covalent or non-covalent association, to complexing agents, including lipophilic derivatives thereof, or to proteinaceous macromolecules. Complexing agents can include, for example, diethylenetriaminepentaacetic acid (DTPA), ethylenediaminetetraacetic acid (EDTA), 1,4,7,10-tetraazacyclododecane-N,N',N",N'''-tetraacetic acid (DOTA), 1,4,7,10-tetraazacyclododecane-N,N',N"-triacetic acid (DOTA), 3,6,9-triaza-12-oxa-3,6,9-tricarboxymethylene-10-carboxy-13-phenyltrideca-noic acid (B-19036), hydroxybenzylethylenediamine diacetic acid (HBED), N,N'-bis(pyridoxyl-5-phosphate)ethylene diamine, N,N'-diacetate (DPDP), 1,4,7-triazacyclononane-N,N',N"-triacetic acid (NOTA), 1,4,8,11-tetraazacyclotetradecane-N,N',N", N'''-tetraacetic acid (TETA), kryptands (macrocyclic complexes), and desferrioxamine. In some embodiments, the complexing agents are EDTA, DTPA, DOTA, DO3A and kryptands, such as DTPA. Lipophilic complexes can include alkylated derivatives of the complexing agents EDTA, DOTA, for example, N,N'-bis(carboxydecylamidomethyl-N-2,3-dihydroxypropyl)ethylenediamine-N—,N'-diacetate (EDTA-DDP); N,N'-bis-(carboxyoctadecylamidomethyl-N-2,3-dihydroxypropypethylenediamin-e-N,N'-diacetate (EDTA-ODP); and N,N'-Bis(carboxy-laurylamidomethyl-N-2,3-dihydroxypropyl)ethylenediamine-N,N'-diacetate (EDTA-LDP). Proteinaceous macromolecules can include, for example, albumin, collagen, polyarginine, polylysine, polyhistidine, γ-globulin and β-globulin. In certain embodiments, the proteinaceous macromolecule is an albumin, polyarginine, polylysine or polyhistidine. Suitable complexes therefore include Mn(II)-DTPA, Mn(II)-EDTA, Mn(II)-DOTA, Mn(II)-DO3A, Mn(II)-kryptands, Gd(III)-DTPA, Gd(III)-DOTA, Gd(III)-DO3A, Gd(III)-kryptands, Cr(III)-EDTA, Cu(II)-EDTA, or iron-desferrioxamine. In specific embodiments, the complexes are Mn(II)-DTPA or Gd(III)-DTPA.

Exemplary superparamagnetic contrast agents suitable for use in the compositions herein include metal oxides and sulfides which experience a magnetic domain, ferro- or ferrimagnetic compounds, such as pure iron, magnetic iron oxide, such as magnetite, $\gamma$-$Fe_2O_3$, $Fe_3O_4$, manganese ferrite, cobalt ferrite and nickel ferrite. MR whole body imaging may then be employed to rapidly screen the body, for example, for thrombosis, and ultrasound may be applied, if desired, to aid in thrombolysis.

The contrast agents, such as the paramagnetic and superparamagnetic contrast agents described above, may be employed as a component within the PGMs and/or stabilizing materials. With respect to vesicles, the contrast agents may be entrapped within the internal void thereof, administered as a solution with the PGMs, incorporated with any additional stabilizing materials, or coated onto the surface or membrane of the vesicle. Mixtures of any one or more of the paramagnetic agents and/or superparamagnetic agents in the present compositions may be used. The paramagnetic and superparamagnetic agents may also be coadministered separately, if desired.

If desired, the paramagnetic or superparamagnetic agents may be delivered as alkylated or other derivatives incorporated into the compositions, especially the lipidic walls of the PGMs. In particular, the nitroxides 2,2,5,5-tetramethyl-1-pyrrolidinyloxy, free radical and 2,2,6,6-tetramethyl-1-piperidinyloxy, free radical, can form adducts with long chain fatty acids at the positions of the ring which are not occupied by the methyl groups via a variety of linkages, including, for example, an acetyloxy linkage.

The PGMs provided herein may serve not only as effective carriers of the superparamagnetic agents described above, but also may improve the effect of the susceptibility contrast agents. Superparamagnetic contrast agents include metal oxides, particularly iron oxides but including manganese oxides, and as iron oxides, containing varying amounts of manganese, cobalt and nickel which experience a magnetic domain.

The iron oxides may simply be incorporated into the stabilizing materials and/or PGMs. In specific embodiments, the iron oxides may be incorporated into the PGMs, for example, by being entrapped within the interior of the PGMs.

Kits

Also provided herein are pharmaceutical packs and kits comprising one or more containers filled with one or more of the ingredients of the compositions provided herein. The kits can comprise, for example, PGMs and one or more additional components, wherein one, two, three or more of the components can be in one, two, three or more vials. In certain embodiments the PGMs are provided in the form of a dry powder. In other embodiments, the PGMs are provided in a biocompatible carrier, for example as an emulsion or suspension.

In certain embodiments, the container is a syringe (e.g., a polycarbonate, polypropylene, or cyclic olefin polymer (COP) syringe). In specific embodiments, the syringe has low moisture loss, which can result in an increased shelf-life (e.g., 2 to 3 years or longer) for pre-filled syringe embodiments of the kits provided herein. In a specific embodiment, PGMs provided herein are contained within a sterile syringe, such as a sterile pre-filled syringe (e.g., a 20 cc syringe), that is optionally provided in a peel-away pouch. In certain embodiments, the syringe comprises about 1 ml, 2 ml, 3 ml or 4 ml of the PGMs in a pharmaceutically acceptable carrier, such as saline (e.g., a non-pyrogenic or pyrogen-free, sterile physiological saline).

In other embodiments, the PGMs provided herein are contained within a vial. In specific embodiments, the vial is a glass vial with a screw-off cap (e.g., a 5 ml glass vial), that is optionally packaged in a peel-away pack comprising one or more additional vials. In specific embodiments, the vial comprises 1 ml or 2 ml of the PGMs in a pharmaceutically acceptable carrier, such as saline (e.g., a non-pyrogenic or pyrogen-free, sterile physiological saline).

In one kit format embodiment, the PGMs provided herein are present in a liquid, physiologically compatible solution in one vial. In another kit format, the PGMs of the provided herein are present in dry form in one vial. In certain kit formats comprising multiple components in multiple vials, the contents of the vials can be mixed together prior to or concurrently with administration. In some embodiments, the PGMs are suspended in a suitable liquid prior to administration, or optionally a second vial is provided, which contains the injectable solution and the contents of both vials are combined prior to administration or concurrently with administration.

Finally, in another kit format the PGMs provided herein are present in one vial and a second vial contains a pharmaceutically acceptable solution comprising the contrast agent. The PGMs can then be mixed together with the contrast agent, for example, prior to or concurrently with administration.

The following examples are offered by way of illustration, and not by way of limitation.

EXAMPLES

Example 1. Synthesis of Phosphate Glass Microspheres Using a Polyphosphate Coacervate Materials & Methods—Step 1—Preparation of Sodium Polyphosphate (NaPP):

A binary sodium phosphate glass with $Na_2O/P_2O_5$ ratio of 1.04 is prepared; 80 g of $NaH_2PO_4 \cdot H_2O$ powder is mixed with 1.229 g of $Na_2CO_3$ powder in a capped container overnight inside a rotary mixer. The mixture is added to a Pt crucible and heated from 25° C. to 900° C. at 1 hr 30 min and kept at 900° C. for 4 hr, then quenched on a copper plate. 1 g of this glass dissolved in DI-$H_2O$ and then 0.9 mL of this solution was added to 0.1 mL of $D_2O$ inside an NMR tube and the number average degree of polymerization (Dp) was determined to be 38. 40 g of the glass was dissolved in 300 mL of DI-$H_2O$ overnight, and subsequently the solution was paper filtered and the volume adjusted to 400 mL. This solution is serial-fractioned by acetone addition resulting in 7 fractions. The Dp of each fraction is determined by NMR, and their phosphate content per weight is determined by ICP-OES.

Figure 2:
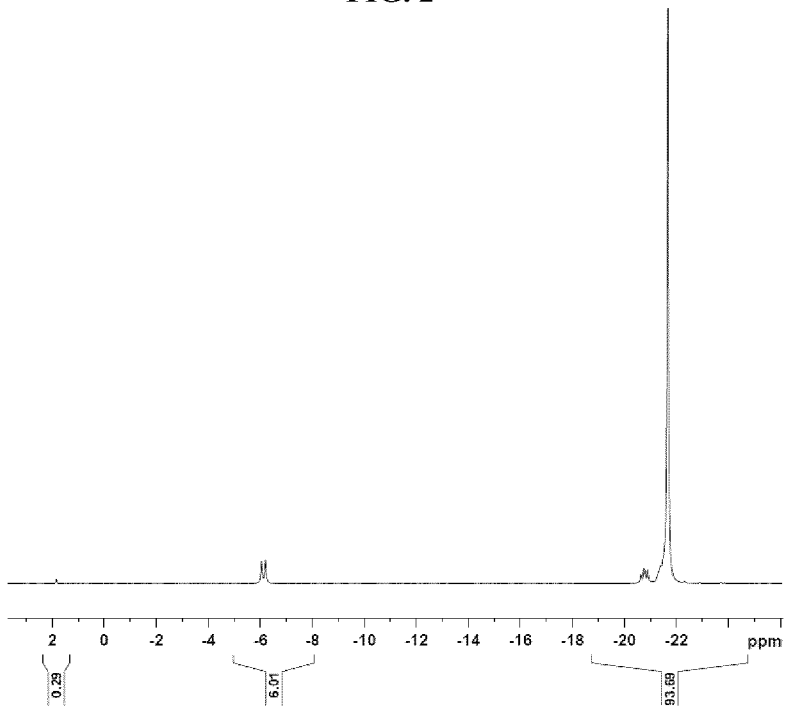
FIG. 2. depicts a liquid $^{31}$P-NMR spectra of a liquid NaPP (sodium polyphosphate) in accordance with the embodiments of the present application.

The 6th fraction of NaPP is used for the following PGM preparation because of the lower viscosity of the coacervates that are obtained using this fraction. Lower viscosity facilitates formation of PGM. FIG. 2 shows the liquid $^{31}$P-NMR of this fraction. It has a Dp of 30.

Step 2—Determining if Cu-Loaded Coacervate can be Prepared

Figure 3A:
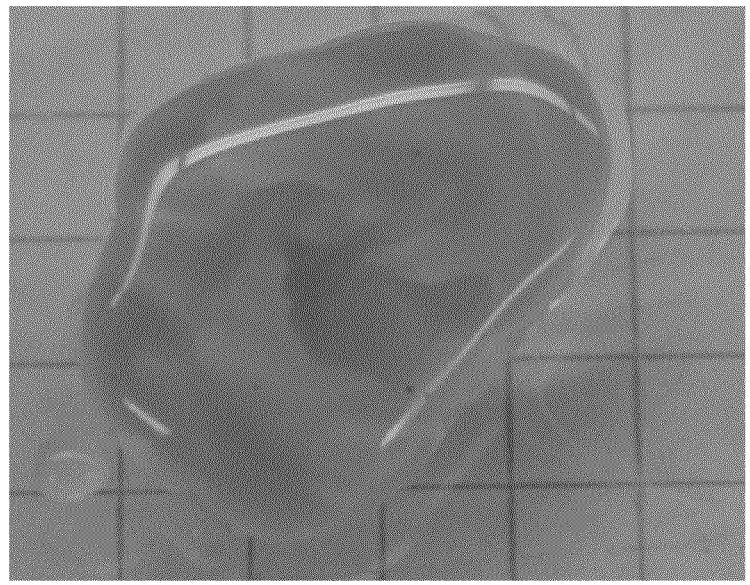
FIG. 3A depicts a photograph of Cu & Ca polyphosphate coacervate in accordance with the embodiments of the present application.
Figure 3B:
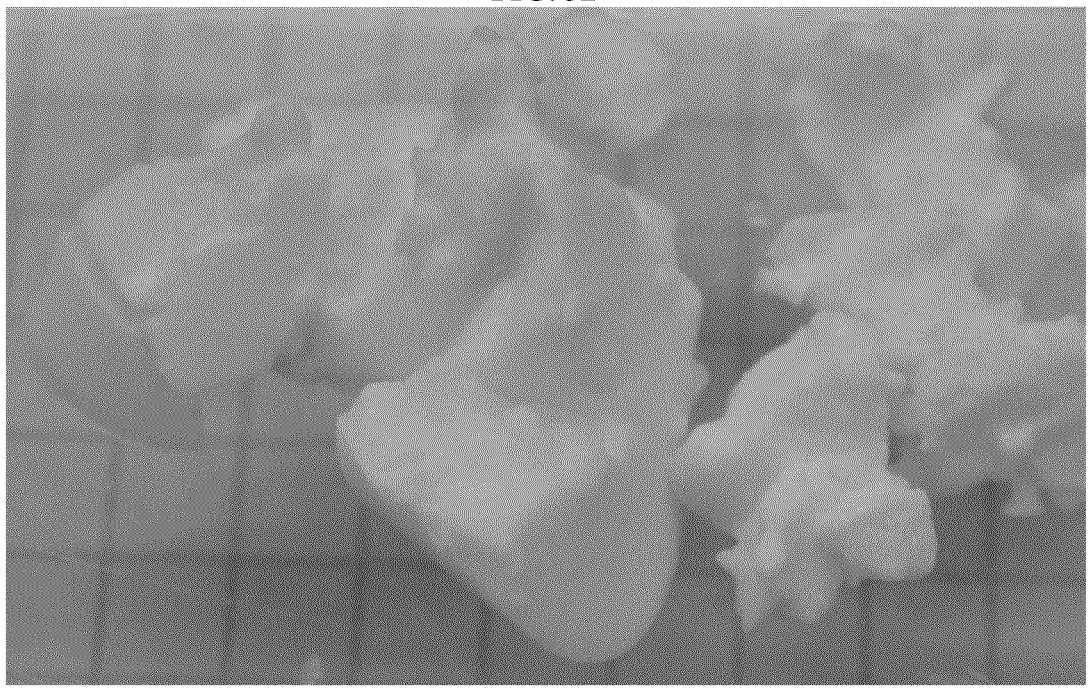
FIG. 3B depicts a photograph of Ba & Ca polyphosphate flocculates in accordance with the embodiments of the present application.
Figure 4A:
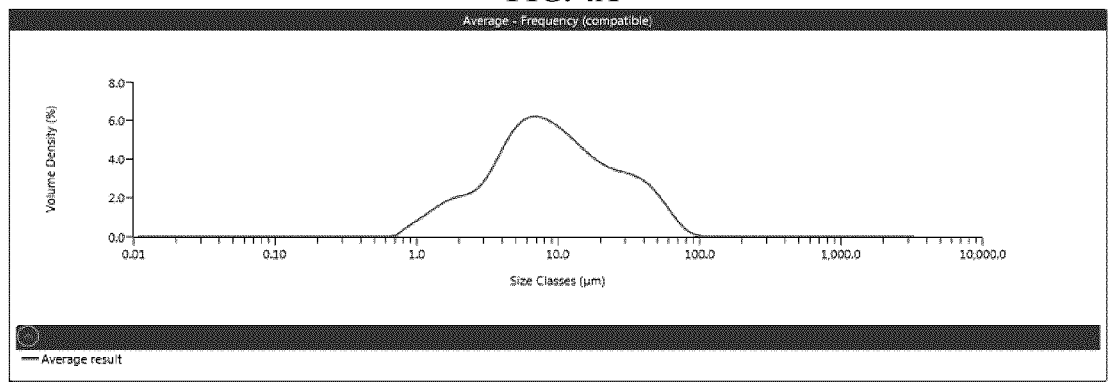
FIG. 4A depicts the average particle size of 0% Cu-loaded PGMs determined using a particle size analyzer (Mastersizer 3000, Malvern Instruments Ltd) with ethylene glycol as the dispersant.
Figure 4B:
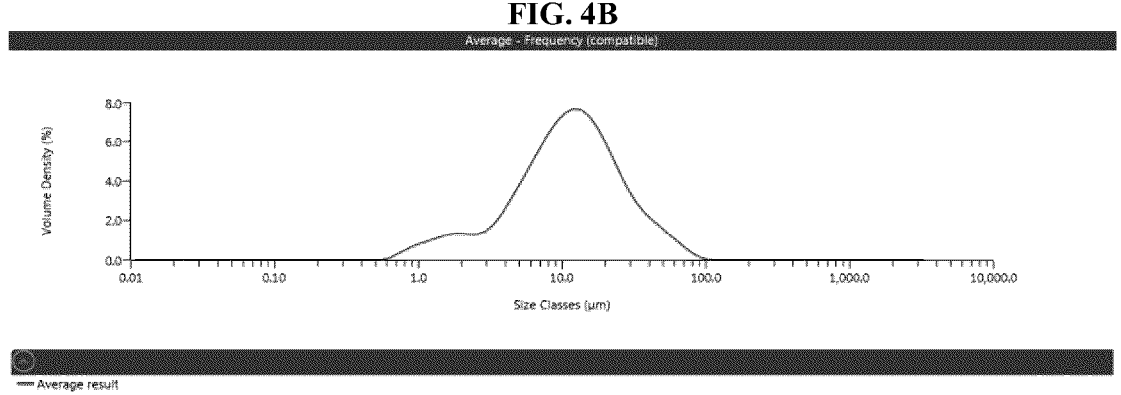
FIG. 4B depicts the average particle size of 2% Cu-loaded PGMs determined using a particle size analyzer (Mastersizer 3000, Malvern Instruments Ltd) with ethylene glycol as the dispersant.
Figure 4C:
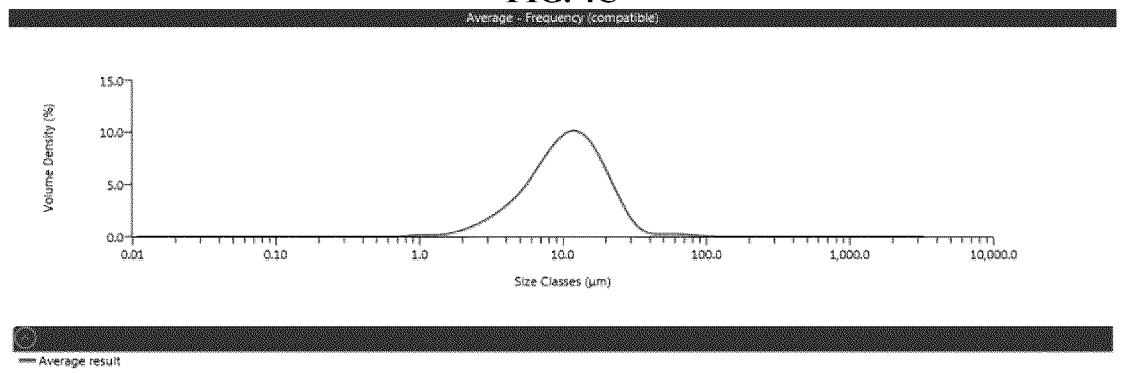
FIG. 4C depicts the average particle size of 5% Cu-loaded PGMs determined using a particle size analyzer (Mastersizer 3000, Malvern Instruments Ltd) with ethylene glycol as the dispersant.
Figure 4D:
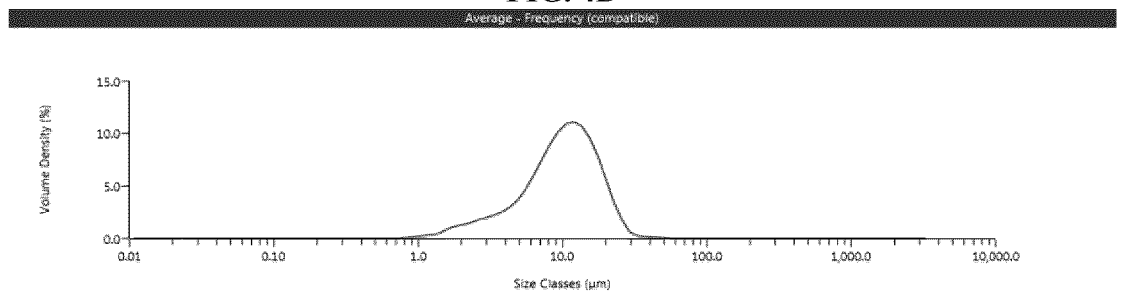
FIG. 4D depicts the average particle size of 10% Cu-loaded PGMs determined using a particle size analyzer (Mastersizer 3000, Malvern Instruments Ltd) with ethylene glycol as the dispersant.
Figure 4D:
Figure 5A:
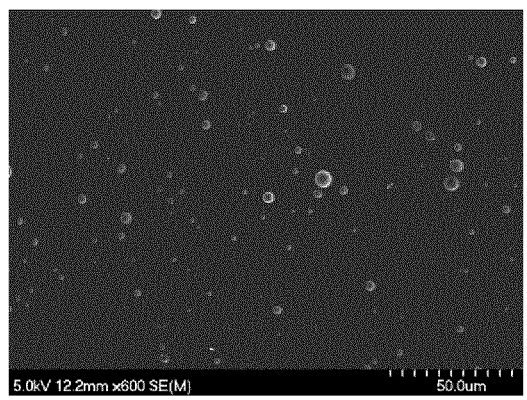
FIG. 5A depicts a photomicrograph of PGMs obtained via scanning electron microscopy of 0% Cu-loaded PGMs at low magnification.
Figure 5B:
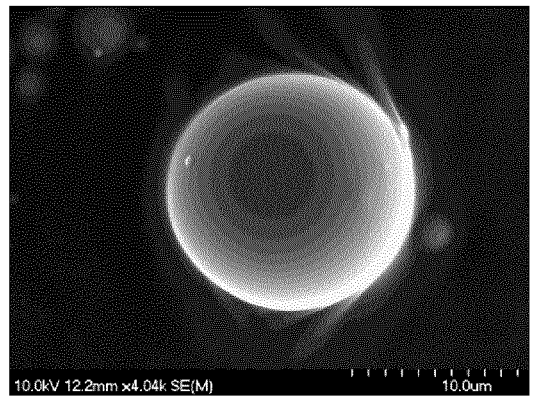
FIG. 5B depicts a photomicrograph of PGMs obtained via scanning electron microscopy of 0% Cu-loaded PGMs at high magnification.
Figure 5C:
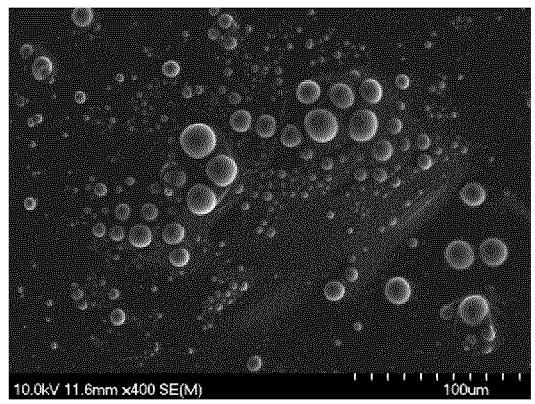
FIG. 5C depicts a photomicrograph of PGMs obtained via scanning electron microscopy of 2% Cu-loaded PGMs at low magnification.
Figure 5D:
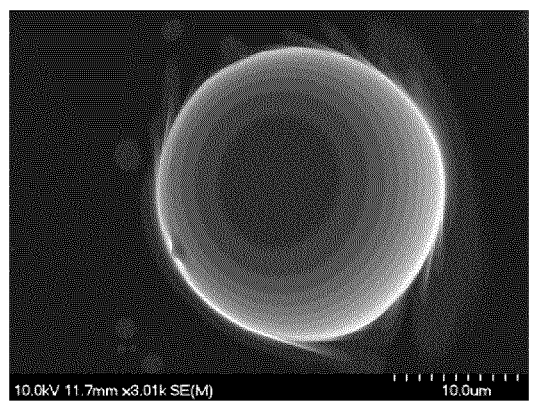
FIG. 5D depicts a photomicrograph of PGMs obtained via scanning electron microscopy of 2% Cu-loaded PGMs at high magnification.
Figure 5E:
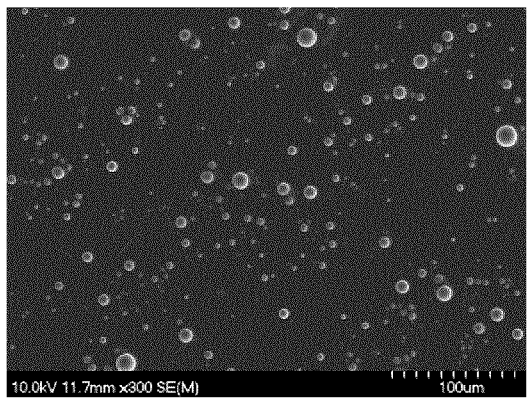
FIG. 5E depicts a photomicrograph of PGMs obtained via scanning electron microscopy of 5% Cu-loaded PGMs at low magnification.
Figure 5F:
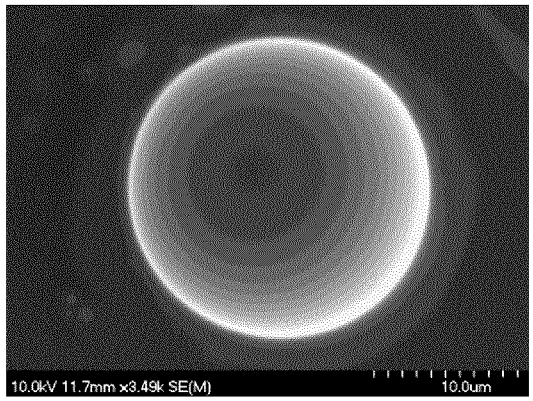
FIG. 5F depicts a photomicrograph of PGMs obtained via scanning electron microscopy of 5% Cu-loaded PGMs at high magnification.
Figure 5G:
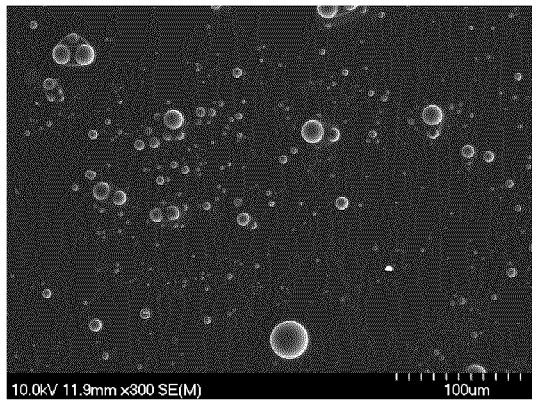
FIG. 5G depicts a photomicrograph of PGMs obtained via scanning electron microscopy of 10% Cu-loaded PGMs at low magnification.
Figure 5H:
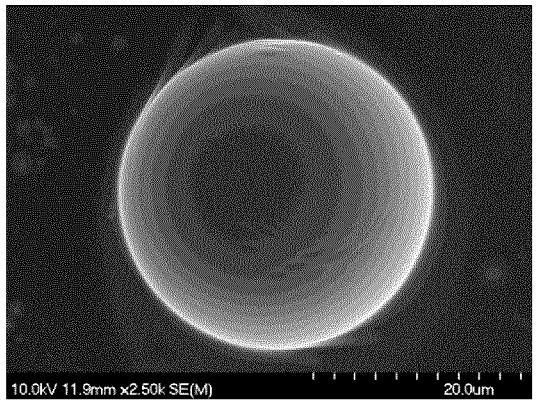
FIG. 5H depicts a photomicrograph of PGMs obtained via scanning electron microscopy (SEM) of 10% Cu-loaded PGMs at high magnification.
Figure 7D:
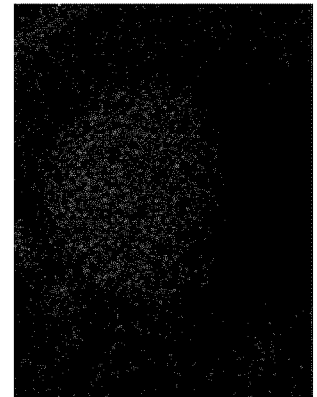
FIG. 7D depicts a photomicrograph of 2% Cu-loaded PGMs obtained using energy-dispersive X-ray spectroscopy (EDX) highlighting the distribution of P.
Figure 6C:
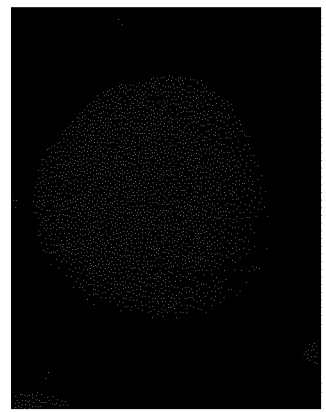
FIG. 6C depicts a photomicrograph of 0% Cu-loaded PGMs obtained using energy-dispersive X-ray spectroscopy (EDX) highlighting the distribution of P.
Figure 7C:
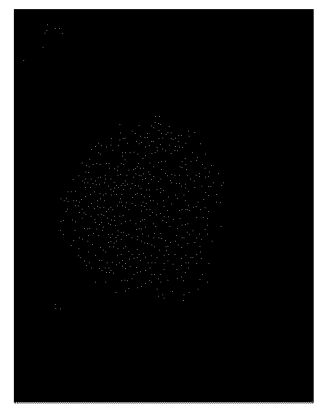
FIG. 7C depicts a photomicrograph of 2% Cu-loaded PGMs obtained using energy-dispersive X-ray spectroscopy (EDX) highlighting the distribution of Cu.
Figure 6B:
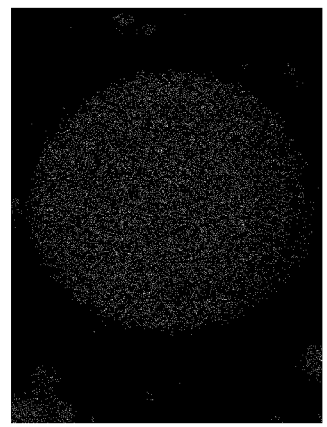
FIG. 6B depicts a photomicrograph of 0% Cu-loaded PGMs obtained using energy-dispersive X-ray spectroscopy (EDX) highlighting the distribution of Ca.
Figure 7B:
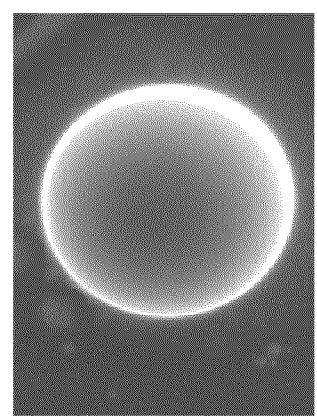
FIG. 7B depicts a photomicrograph of 2% Cu-loaded PGMs obtained using energy-dispersive X-ray spectroscopy (EDX) highlighting the distribution of Ca.
Figure 6A:
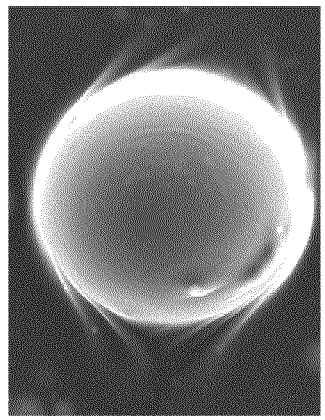
FIG. 6A depicts a photomicrograph of 0% Cu-loaded PGMs obtained using SEM.
Figure 7A:
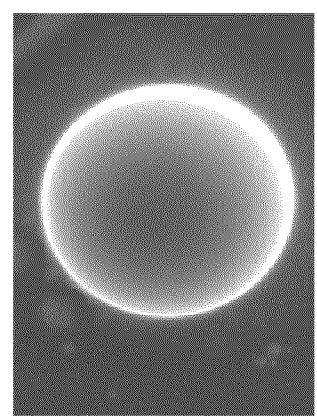
FIG. 7A depicts a photomicrograph of 2% Cu-loaded PGMs obtained using SEM.
Figure 8D:
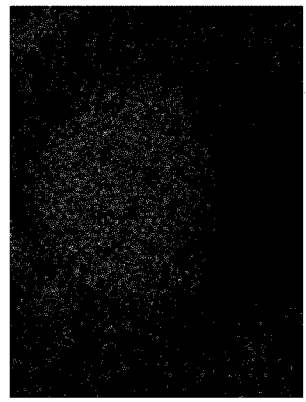
FIG. 8D depicts a photomicrograph of 5% Cu-loaded PGMs obtained using energy-dispersive X-ray spectroscopy (EDX) highlighting the distribution of P.
Figure 9D:
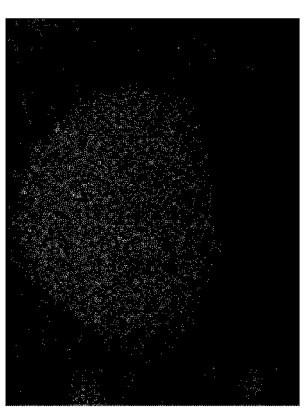
FIG. 9D depicts a photomicrograph of 10% Cu-loaded PGMs obtained using energy-dispersive X-ray spectroscopy (EDX) highlighting the distribution of P.
Figure 8C:
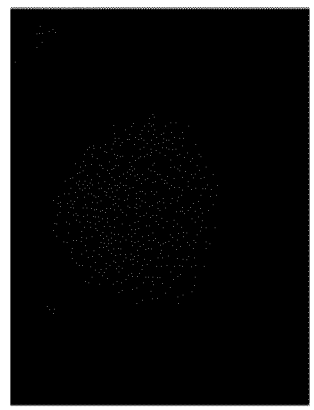
FIG. 8C depicts a photomicrograph of 5% Cu-loaded PGMs obtained using energy-dispersive X-ray spectroscopy (EDX) highlighting the distribution of Cu.
Figure 9C:
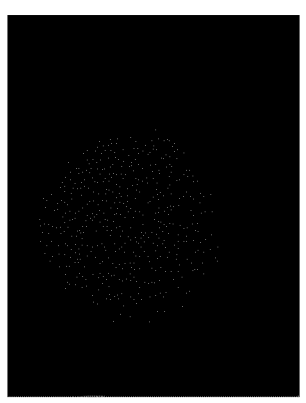
FIG. 9C depicts a photomicrograph of 10% Cu-loaded PGMs obtained using energy-dispersive X-ray spectroscopy (EDX) highlighting the distribution of Cu.
Figure 8B:
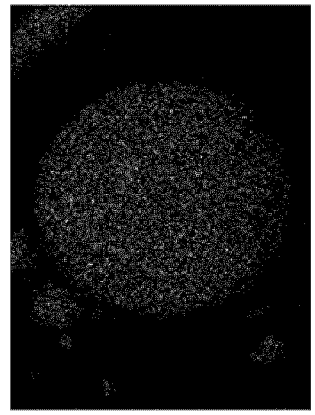
FIG. 8B depicts a photomicrograph of 5% Cu-loaded PGMs obtained using energy-dispersive X-ray spectroscopy (EDX) highlighting the distribution of Ca.
Figure 9B:
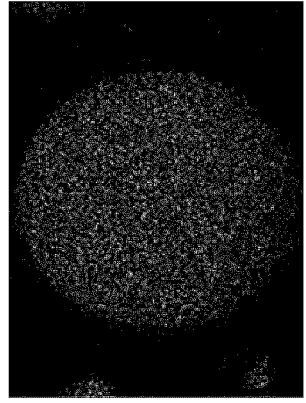
FIG. 9B depicts a photomicrograph of 10% Cu-loaded PGMs obtained using energy-dispersive X-ray spectroscopy (EDX) highlighting the distribution of Ca.
Figure 8A:
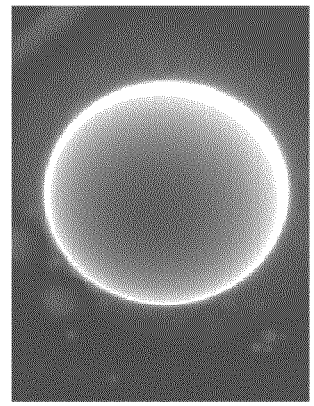
FIG. 8A depicts a photomicrograph of 5% Cu-loaded PGMs obtained using SEM.
Figure 9A:
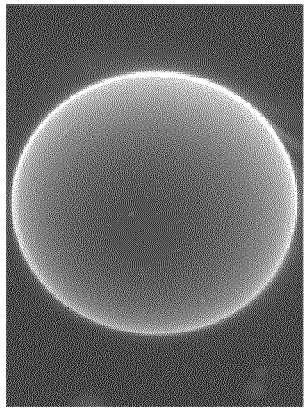
FIG. 9A depicts a photomicrograph of 10% Cu-loaded PGMs obtained using SEM.

To determine if coacervate can be prepared, the desired cations are added to the NaPP solution and mixed. If the precipitate that is obtained has liquid-like properties (i.e. coacervate) as shown in FIG. 3A they can be used for PGM preparation, but if they flocculate and lack liquid-like properties as shown in FIG. 3B they cannot be used for PGM preparation. A series of Cu-loaded precipitates were prepared by dissolving 0.150 g of the prepared NaPP in 15 mL DI-$H_2O$ (5 vials for each NaPP), followed by addition of 0.015 mL, 0.030 mL, 0.075 mL, 0.105 mL, or 0.150 mL 1M Cu solution (prepared from $CuCl_2 \cdot 2H_2O$) and 0.721 mL, 0.706 mL, 0.662 mL, 0.633 mL, or 0.588 mL 1M Ca solution (prepared from $CaCl_2 \cdot 2H_2O$) to yield 1%, 2%, 5%, 7% or 10% Cu/P precipitates, respectively. The precipitates were collected and visually examined to determine if they had liquid-like properties so they can be classified as coacervates. All coacervate were blue in color (e.g. FIG. 3A); the more Cu incorporated in the coacervate, the more intense the color. Under microscope examination, there is no sign of any discrete particles and they look like a continuous homogenous mass. These observations show that even loading as high as 10% Cu/P allows for coacervate formation and subsequent preparation of the corresponding PGMs. The more Cu the coacervate has the lower is its viscosity. We will show in the next step that coacervates with Cu/P mole ratios higher than 10% can also be obtained and can be used for polyphosphate glass microsphere preparation.

Step 3—Preparing PGM Using Cu-Loaded Coacervate

PGM batches with 0%, 2%, 5%, 10% and 100% Cu/P theoretical loading (defined by the Cu/P, with 100% theoretical loading having a Cu/P=1) were prepared as follows. For each batch, 1.5 g of NaPP with Dp of 30 was dissolved in 375 mL DI-$H_2O$. Subsequently, 0 mL, 0.283 mL, 0.709 mL, 1.417 mL, or 14 mL 1M Cu solution (prepared from $CuCl_2 \cdot 2H_2O$) was added, followed by 7.083 mL, 6.800 mL, 6.375 mL, 5.666 mL, or 7 mL 1M Ca (prepared from $CaCl_2 \cdot 2H_2O$) and mixed for 5 min resulting in coacervates having, respectively, 0%, 2%, 5%, 10%, or 100% Cu/P theoretical loading and overall theoretical divalent cation to phosphorus mole ratio of 50% (with the exception of the 100% Cu-loaded formulation, which has theoretical divalent cation to phosphorus mole ratio of 150%). The coacervates were collected after centrifuging the solution inside 50 mL falcon tubes at 4400 rpm for 10 min.

Simultaneously in a fume hood 4.5 g polycaprolactone (PCL, Mn of 80,000 g/mol) was added to 150 mL chloroform and mixed with an overhead stirrer at 500 rpm for 30 min, then another 4.5 g PCL was added to the solution and mixing continued until a clear solution was obtained. To this solution 1 mL span80 was added as an emulsifier. 0.5 mL of DI-$H_2O$ is also added to this solution prior to coacervate addition as it helps with PGM preparation. The coacervate that was collected is added to this solution and the emulsion mixed at 2000 rpm for 1 hr 30 mins. During this time chloroform volume needs to be continuously adjusted because some of the chloroform evaporates. Subsequently, 300 mL acetone was added and the mixing continued at 400 rpm for 3 hr. The mixture containing PGM was then centrifuged at 4400 rpm for 5 min inside 50 mL falcon tubes to collect the PGM and discard the supernatant solution. The PGM were washed twice with chloroform and twice with acetone, then topped with acetone and stored at −8° C. (standard refrigeration). These PGM were sieved in the presence of acetone on a vibrating table using 3" stainless steel sieves (Gilson Company, Inc) into 3 size range fractions (<20 µm, 20-106 µm, >106 µm), then topped with acetone and kept inside a 50 mL falcon tube at ~8° C.

Step 4—Characterizing Prepared PGMs

Particle size of these PGMs was determined using a particle size analyzer (Mastersizer 3000, Malvern Instruments Ltd) with ethylene glycol as the dispersant. As an example, the particle size distribution of four of the <20 µm PGMs are shown in FIGS. 4A-4D (average of 10 measurements). The mean size of the PGMs (D[4,3]) are 14.3±1.5, 14.9±0.8, 12.3±1.4, 10.8±0.7 µm for 0, 2, 5 and 10% Cu-loaded PGMs, respectively.

The theoretical and experimental compositions of <20 µm PGMs are reported in Table 1. ICP-OES analyses shows that experimental composition is not identical to theoretical values because some of the divalent cations did not incorporate into the coacervates used for PGM preparation. Note that for the '100%' Cu/P sample in particular, no coacervate was formed until enough $CaCl_2$ was added to achieve coacervate formation, yielding an experimental Cu/P mole ratio of ~25%. In all formulations, the total experimental divalent cation/P mole ratio is approximately 0.47.

TABLE 1

PGM theoretical and experimental mole ratios.

| PGM composition | Theoretical mole ratio | | Experimental mole ratio determined by ICP-OES | |
|---|---|---|---|---|
| | $Cu^{2+}/P$ | $Ca^{2+}/P$ | $Cu^{2+}/P$ | $Ca^{2+}/P$ |
| 0% $Cu^{2+}$-loaded PGM | 0.00 | 0.50 | NA | 0.47 ± 0.00 |
| 2% $Cu^{2+}$-loaded PGM | 0.02 | 0.48 | 0.02 ± 0.00 | 0.45 ± 0.01 |
| 5% $Cu^{2+}$-loaded PGM | 0.05 | 0.45 | 0.04 ± 0.00 | 0.43 ± 0.00 |
| 10% $Cu^{2+}$-loaded PGM | 0.10 | 0.40 | 0.07 ± 0.00 | 0.39 ± 0.00 |
| 100% $Cu^{2+}$-loaded PGM | 1.00 | 0.50 | 0.25 ± 0.01 | 0.21 ± 0.01 |

Scanning electron microscopy (SEM) images of <20 µm PGMs were obtained by putting a drop of PGM acetone solution on an SEM stub covered by a carbon tape; the stubs are then coated by carbon and imaged using a Hitachi S-4700 FEG Scanning Electron Microscope. See FIGS. 5A-5D. These figures show the SEM of four of the PGMs at high and low magnifications. Independent of the composition, PGMs are all highly spherical with very smooth surfaces.

In addition, energy-dispersive X-ray spectroscopy (EDX) was also performed on PGMs while they were being imaged by SEM as shown in FIGS. 6A-6C, 7A-7D, 8A-8D, and 9A-9D. These figures show the results of EDX analyses, demonstrating the uniform distribution of Ca, Cu and P in PGMs. Atomic percentages determined by EDX were in agreement with ICP-OES results.

Step 5—Stabilizing PGM by an Ion-Exchange Process

PGM prepared here aggregate in the presence of water and transform back to the coacervate. Preliminary studies have shown that replacing Ca with Ba stabilizes the PGM, preventing them from aggregating in the presence of water. Therefore, here we wanted to investigate the possibility of stabilizing Cu-loaded PGM by an ion exchange process in which Ca and/or Cu in the PGM is substituted for Ba. Initial studies using 1M Ba (prepared from $BaCl_2 \cdot 2H_2O$) indicated that ion exchange resulting in a Ba/P mole ratio of ~0.35 or higher is required to prevent PGM aggregation, with stabilization not achieved until 5 days in this higher Ba concentration solution.

Subsequent studies were carried out at lower Ba concentration to determine if this had an effect on the rate of ion-exchange. In some examples, 0.5 mL of <20 µm Ca-only (0% Cu-loaded) PGM was added to seven 2 mL Eppendorf tubes, centrifuged and the acetone discarded. Subsequently, 2 mL of 0.5, 0.2, 0.1, 0.05, 0.02, 0.01, or 0.002M Ba solutions were added to each tube and kept on rotary mixer at ~8 C. They were checked after 3 hr, 24 hr and 4 days visually and under the microscope. No aggregation was observed and all PGMs held their shapes at all concentrations even as low as 0.002M Ba. A larger size PGM was also evaluated. Here, 2 mL of 0.5M or 0.01M Ba was added to 20-106 µm 5% Cu-loaded PGM and followed up for 3 days. No coacervate formed after 3 hr and the PGM shapes remained intact. After 3 days at 8° C. no coacervate was observed in the tube containing PGM at 0.5M Ba solution, but a large coacervate mass was noted in the tube containing PGM at 0.01M Ba solution. A sample of solution was observed under microscope and most of the PGM were broken and had lost their spherical form. Conclusively for large PGM, low Ba solution can prevent aggregation only for a short-term.

Figure 10A:
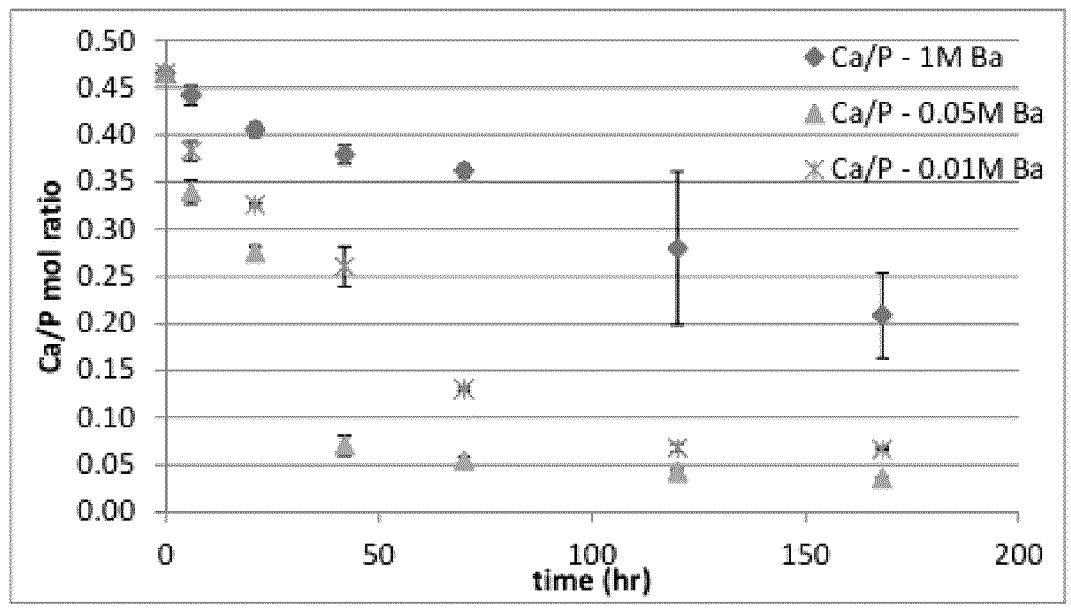
FIG. 10A depicts a graph illustrating the change in the Ca/P mole ratio versus time for ion exchange of Cu to Ba performed at the three different Ba concentrations.
Figure 10B:
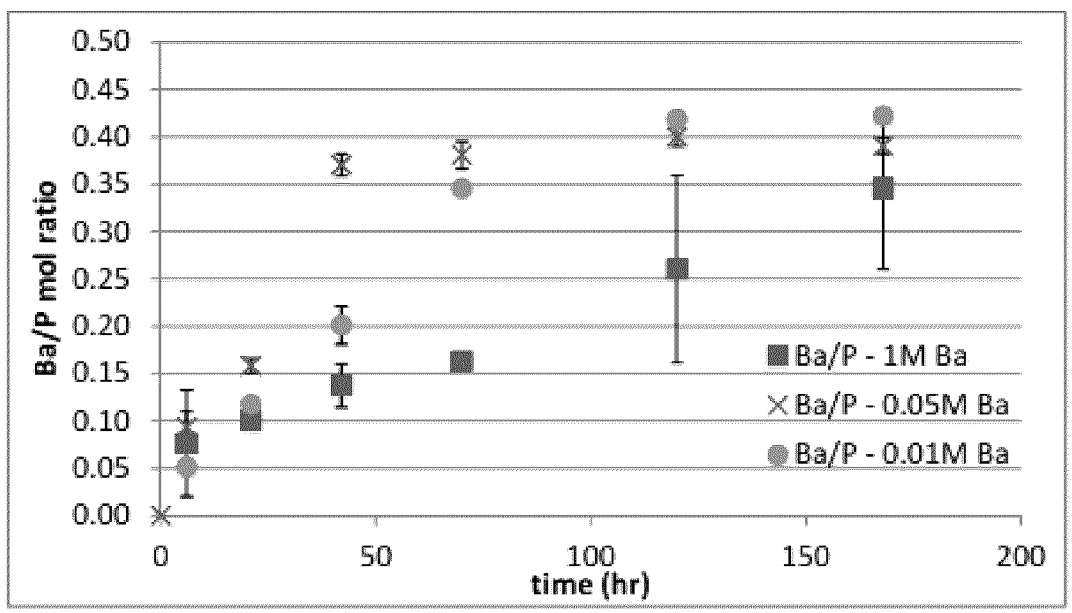
FIG. 10B depicts a graph illustrating the change in the Ba/P mole ratio versus time for ion exchange of Cu to Ba performed at the three different Ba concentrations.
Figure 12A:
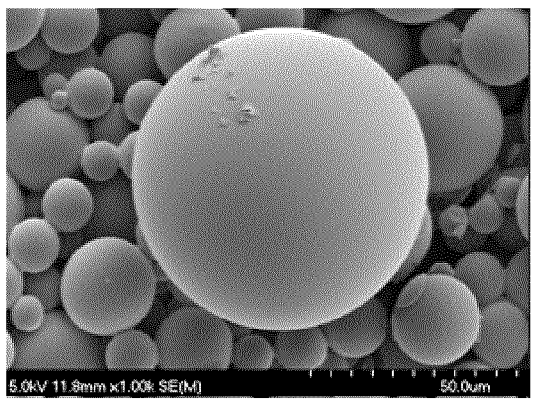
FIG. 12A depicts a SEM photomicrograph of small minocycline loaded calcium polyphosphate microspheres at various magnifications.
Figure 12B:
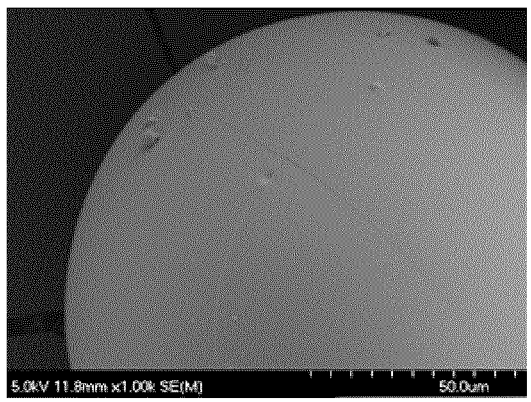
FIG. 12B depicts a SEM photomicrograph of large minocycline loaded calcium polyphosphate microspheres at various magnifications.
Figure 12C:
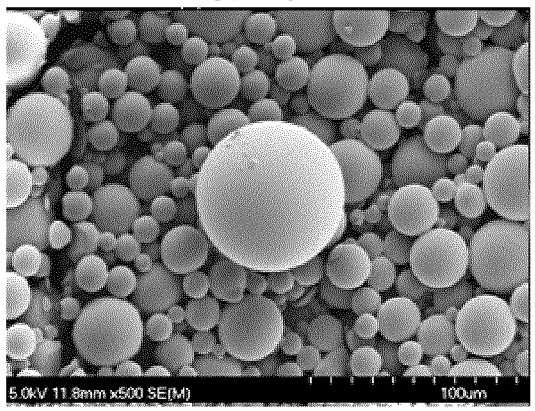
FIG. 12C depicts a SEM photomicrograph of small minocycline loaded calcium polyphosphate microspheres at various magnifications.
Figure 12D:
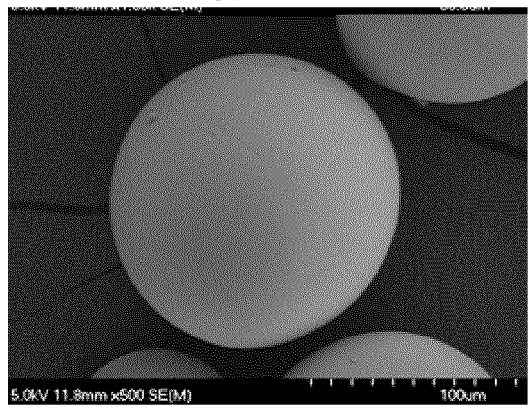
FIG. 12D depicts a SEM photomicrograph of large minocycline loaded calcium polyphosphate microspheres at various magnifications.

Based on these results a more extensive ion-exchange study of PGM in the presence of 1 M Ba, 0.05M Ba or 0.01M Ba solutions was undertaken. Eppendorf tubes containing only <20 µm Ca-only (0% Cu-loaded) PGM were prepared and 2 mL of 0.05M Ba or 0.01M Ba was added, with tubes maintained at ~8 C on a rotary mixer for 7 days. At each time point they were checked for aggregation and also their ion-exchange was determined by ICP-OES. Table 2 shows the results shown in FIGS. 10A and 10B, highlighting the comparison of the results of the ion exchange at the three different Ba concentrations. Clearly, ion exchange occurs at faster rates at lower Ba concentration. At 0.05M Ba the rate of ion exchange is the fastest, with the Ba/P threshold of ~0.35 already surpassed at 42 hr.

TABLE 2

PGM ion exchange in the presence of 1M, 0.05M, and 0.01M Ba solutions.

| PGM batch | Time | Ca/P | Cu/P | Ba/P | Aggregation |
|---|---|---|---|---|---|
| 0% Cu-loaded PGM in 1M Ba | 0 hr | 0.47 ± 0.00 | N/A | 0.00 ± 0.00 | All 3 tubes |
| | 6 hr | 0.44 ± 0.01 | N/A | 0.08 ± 0.06 | All 3 tubes |
| | 21 hr | 0.41 ± 0.01 | N/A | 0.10 ± 0.01 | All 3 tubes |
| | 42 hr | 0.38 ± 0.01 | N/A | 0.14 ± 0.02 | All 3 tubes |
| | 70 hr | 0.36 ± 0.01 | N/A | 0.16 ± 0.01 | All 3 tubes |

TABLE 2-continued

PGM ion exchange in the presence of 1M, 0.05M, and 0.01M Ba solutions.

| PGM batch | Time | Ca/P | Cu/P | Ba/P | Aggregation |
|---|---|---|---|---|---|
| | 5 days | 0.28 ± 0.08 | N/A | 0.26 ± 0.10 | 2 out of 3 tubes |
| | 7 days | 0.21 ± 0.05 | N/A | 0.35 ± 0.09 | None of 3 tubes |
| 0% Cu-loaded PGM in 0.05M Ba | 0 hr | 0.47 ± 0.00 | N/A | 0.00 ± 0.00 | All 3 tubes |
| | 6 hr | 0.34 ± 0.01 | N/A | 0.09 ± 0.02 | All 3 tubes |
| | 21 hr | 0.27 ± 0.01 | N/A | 0.16 ± 0.01 | All 3 tubes |
| | 42 hr | 0.07 ± 0.01 | N/A | 0.37 ± 0.01 | None of 3 tubes |
| | 70 hr | 0.05 ± 0.00 | N/A | 0.38 ± 0.01 | None of 3 tubes |
| | 5 days | 0.04 ± 0.00 | N/A | 0.40 ± 0.01 | None of 3 tubes |
| | 7 days | 0.04 ± 0.00 | N/A | 0.39 ± 0.01 | None of 3 tubes |
| 0% Cu-loaded PGM in 0.01M Ba | 0 hr | 0.47 ± 0.00 | N/A | 0.00 ± 0.00 | All 3 tubes |
| | 6 hr | 0.38 ± 0.01 | N/A | 0.05 ± 0.01 | All 3 tubes |
| | 21 hr | 0.33 ± 0.00 | N/A | 0.12 ± 0.00 | All 3 tubes |
| | 42 hr | 0.26 ± 0.02 | N/A | 0.20 ± 0.02 | All 3 tubes |
| | 70 hr | 0.13 ± 0.00 | N/A | 0.35 ± 0.00 | None of 3 tubes |
| | 5 days | 0.07 ± 0.00 | N/A | 0.42 ± 0.00 | None of 3 tubes |
| | 7 days | 0.07 ± 0.00 | N/A | 0.42 ± 0.00 | None of 3 tubes |

A preliminary ion-exchange study of <20 μm Ca-only (0% Cu-loaded) PGM in presence of 0.05M Sr demonstrated that 7 days is required for PGM stabilization.

An issue with stabilizing Cu-loaded PGM using the ion-exchange process is that stabilization requires a significant amount of Ba substitution (~35% Ba/P). In order to check if it is possible to retain some Cu even after the ion-exchange process, an ion-exchange study was run using 100% Cu-loaded PGM batch, which in practice has an experimentally determined 25% Cu/P mole ratio (Table 1). Ion exchange was carried out in presence of 0.05M Ba and in two size ranges to determine also the effect of PGM size on the ion exchange rate. FIGS. 11A-11D and Table 3 show the results of this study.

TABLE 3

Ion exchange of 100% Cu-loaded and 0% Cu-loaded PGMs in presence of 0.05M Ba solution.

| PGM batch | Time | Ca/P | Cu/P | Ba/P | Aggregated? |
|---|---|---|---|---|---|
| 100% Cu-loaded PGM (20-106 μm) | 0 hr | 0.22 ± 0.00 | 0.27 ± 0.00 | 0.00 ± 0.00 | All 3 tubes |
| | 3 hr | 0.18 ± 0.00 | 0.21 ± 0.01 | 0.11 ± 0.01 | All 3 tubes |
| | 6 hr | 0.16 ± 0.02 | 0.18 ± 0.02 | 0.16 ± 0.02 | All 3 tubes |
| | 12 hr | 0.09 ± 0.01 | 0.10 ± 0.02 | 0.30 ± 0.03 | 2 out of 3 tubes |
| | 24 hr | 0.04 ± 0.00 | 0.05 ± 0.00 | 0.40 ± 0.01 | None of 3 tubes |
| | 36 hr | 0.03 ± 0.00 | 0.04 ± 0.00 | 0.41 ± 0.01 | None of 3 tubes |
| | 48 hr | 0.03 ± 0.00 | 0.04 ± 0.00 | 0.42 ± 0.00 | None of 3 tubes |
| | 72 hr | 0.03 ± 0.00 | 0.03 ± 0.00 | 0.42 ± 0.00 | None of 3 tubes |
| 100% Cu-loaded PGM (<20 μm) | 0 hr | 0.21 ± 0.01 | 0.25 ± 0.01 | 0.00 ± 0.00 | All 3 tubes |
| | 3 hr | 0.12 ± 0.01 | 0.14 ± 0.01 | 0.22 ± 0.01 | All 3 tubes |
| | 6 hr | 0.06 ± 0.00 | 0.07 ± 0.00 | 0.35 ± 0.01 | 1 out of 3 tubes |
| | 12 hr | 0.03 ± 0.00 | 0.03 ± 0.00 | 0.42 ± 0.01 | None of 3 tubes |
| | 24 hr | 0.02 ± 0.00 | 0.02 ± 0.00 | 0.43 ± 0.01 | None of 3 tubes |
| | 36 hr | 0.01 ± 0.00 | 0.02 ± 0.00 | 0.43 ± 0.00 | None of 3 tubes |
| | 48 hr | 0.01 ± 0.00 | 0.02 ± 0.00 | 0.43 ± 0.00 | None of 3 tubes |
| | 72 hr | 0.01 ± 0.00 | 0.02 ± 0.00 | 0.43 ± 0.00 | None of 3 tubes |
| 0% Cu-loaded PGM (20-106 μm) | 0 hr | 0.46 ± 0.00 | N/A | 0.00 ± 0.00 | All 3 tubes |
| | 3 hr | 0.46 ± 0.00 | N/A | 0.03 ± 0.00 | All 3 tubes |
| | 6 hr | 0.43 ± 0.01 | N/A | 0.06 ± 0.01 | All 3 tubes |
| | 12 hr | 0.39 ± 0.02 | N/A | 0.08 ± 0.02 | All 3 tubes |
| | 24 hr | 0.32 ± 0.03 | N/A | 0.16 ± 0.03 | All 3 tubes |
| | 36 hr | 0.22 ± 0.02 | N/A | 0.26 ± 0.03 | All 3 tubes |
| | 48 hr | 0.10 ± 0.01 | N/A | 0.38 ± 0.00 | None of 3 tubes |
| | 72 hr | 0.07 ± 0.00 | N/A | 0.40 ± 0.00 | None of 3 tubes |
| 0% Cu-loaded PGM (<20 μm) | 0 hr | 0.46 ± 0.00 | N/A | 0.00 ± 0.00 | All 3 tubes |
| | 3 hr | 0.43 ± 0.01 | N/A | 0.05 ± 0.01 | All 3 tubes |
| | 6 hr | 0.31 ± 0.02 | N/A | 0.16 ± 0.03 | All 3 tubes |
| | 12 hr | 0.19 ± 0.02 | N/A | 0.27 ± 0.02 | 2 out of 3 tubes |
| | 24 hr | 0.08 ± 0.00 | N/A | 0.38 ± 0.00 | None of 3 tubes |
| | 36 hr | 0.04 ± 0.00 | N/A | 0.42 ± 0.01 | None of 3 tubes |
| | 48 hr | 0.04 ± 0.00 | N/A | 0.43 ± 0.00 | None of 3 tubes |
| | 72 hr | 0.03 ± 0.00 | N/A | 0.44 ± 0.01 | None of 3 tubes |

The rate of ion-exchange clearly depends on the PGM size, proceeding more quickly for smaller PGM. It is also clear that the ion-exchange rate is faster for "100% Cu-loaded" PGM compared to the Ca-only 0% Cu-loaded PGM; 100% Cu-load PGM (<20 µm) became stable in less than 12 hr at this 0.05M Ba concentration, with a value between 0.03-0.07 Cu/P retained. This suggests it is possible to stabilize the PGM by Ba ion-exchange and still retain a relatively significant amount of Cu.

Visual observation of Ca-only PGM showed that PGM in the size range of 20-106 µm crack and break down during the ion-exchange process. In contrast, <20 µm PGM looked spherical and intact during microscopic examination Visual observation of 100% Cu-loaded PGM showed that PGM in the size range of 20-106 µm do not crack or breakdown. However, their shape becomes distorted, with particles assuming a rain-drop form. <20 µm PGM looked spherical and intact with only a few undergoing distortion.

Step 6—Aggregation in the Presence of Water Miscible Solvents

Lastly it was determined if PGMs aggregate in ethylene glycol-water mixtures. 100% Cu-loaded PGMs in the size range of 20-106 µm were kept at 100%, 75%, 50%, 25% (v. %) ethylene glycol-water mixtures and followed up for 3 days. PGMs retained their shape in 100%, 75% and 50% mixtures, but at 25% they absorbed water and transformed to coacervate. Another way to prevent PGMs from aggregating is to use a mixture of water with such solvents. In addition, ion exchange with ions such as Ba can also be carried out in a mixture of water with such solvents, which may be beneficial in some circumstances. However, this ion-exchange occur more slowly than in pure water; for instance a preliminary study showed that it takes 3-7 days for <20 µm 100% Cu-loaded PGM to become stable in 0.05M Ba solution of 40% ethylene glycol-water, with the same PGM becoming stable in 0.05M Ba water solution in only 12 hr.

Example 2. Drug Loading and Elution from PGMs

Materials and Methods
Sodium Polyphosphate
NaPP was obtained and characterized using the protocol described by Momeni et al. "Synthesis and characterization of different chain length sodium polyphosphates. Journal of Non-Crystalline Solids, 2013. 382 (December 2013): p. 11-17", the disclosure of which is hereby incorporated by reference herein in its entirety. In short, sodium phosphate monophasic monohydrate ($NaH_2PO_4 \cdot H_2O$; Sigma Aldrich, St. Louis, MO, USA) was heated at 700 degrees Celsius in a platinum-5% gold crucible for 1 h, quenched rapidly on a copper plate, and cooled to room temperature. The NaPP glass was then used to make a 10% (w/w) NaPP solution. This solution was then fractioned using serial addition of acetone. Once fractioned, the precipitate was frozen and subsequently freeze-dried. The average degree of polymerization and molecular weight of the fractions was determined using liquid $^{31}P$ nuclear magnetic resonance (NMR), titration and viscosity studies.

Calcium Polyphosphate Precipitation
Precipitation of calcium polyphosphate (CPP) was carried out according to the protocol described by Momeni et al. (as provided in Momeni et al. *Comprehensive study of the chelation and coacervation of alkaline earth metals in the presence of sodium polyphosphate solution*. Langmuir, 2014. 30(18): p. 5256-66, the disclosure of which is incorporated herein by reference in its entirety). At room temperature, 1.5 g of NaPP was added to 250 mL of deionized water and stirred continuously (magnetic stirrer) until fully dissolved. 7.038 mL of 1M $CaCl_2$ was then added to the solution to achieve a 0.5 Ca/P mole ratio. The precipitation reaction went on for 5 minutes with continuous stirring. The CPP precipitate was collected, washed 3 times using deionized water, and stored in a 2 mL Eppendorf tube.

Drug Loading
The CPP coacervate was placed in the freeze-drier for 2 h. 20 mg of minocycline was dissolved in 1.5 mL of deionized water and added to the freeze-dried CPP. This mixture was left in the fridge overnight (12 h) in a scintillation vial. Following refrigeration, the CPP/minocycline was mixed using a hand spatula to allow for homogenous distribution of the minocycline throughout the CPP coacervate. Samples of the minocycline loaded CPP coacervate were collected for drug-loading analysis at this point, and the remaining coacervate was used to produce microspheres.

Microsphere Synthesis
The following was carried out at room temperature, using a glass beaker, and overhead stirrer. While continuously stirring at 200 rpm, 25 g of PCL (thickening agent) was dissolved in 250 mL of chloroform. Stirring speed was increased as the PCL dissolved and the solution became more viscous (up to 500 rpms). Once the PCL was completely dissolved, 1 mL of Span80 (emulsifier) was added to the solution and the stirring speed was increased to 2000 rpm. The minocycline-loaded CPP coacervate (~1 mL) was poured directly into the solution and stirred for 90 minutes. Stirring speed was reduced to 400 rpm and 500 mL of acetone was added. Stirring continued for 3 hours. The solution was then divided equally into 50 mL falcon tubes and centrifuged at 4400 rpm for 1 minute. The last falcon tube filled contained the majority of the large microspheres, while the remaining falcon tubes contained small microspheres. The tubes containing small microspheres were combined. This resulted in a single portion of "large" microspheres and a single portion of "small" microspheres. Supernatant was removed from all tubes and the microspheres were washed as follows: 10 mL of chloroform was added to the microspheres, vortexed for 10 seconds, and centrifuged at 4400 rpm for 1 minutes. The supernatant was removed and the process was repeated once more with chloroform and twice with acetone. Following washing, acetone was added to the tubes containing microspheres and they were stored at 4° C.

Scanning Electron Microscopy and Particle Size Analysis
Samples of "small" and "large" microsphere were plated and carbon coated. Images of these samples at varying magnifications were then obtained using a Hitachi S-4700 FEG scanning electron microscope at 5 kV.

Particle size analysis of the "large" and "small" microsphere samples was carried out using laser diffraction (Malvern Mastersizer 3000).

Drug Loading Analysis
The drug loading of the CPP coacervate, small, and large microspheres were analyzed using spectrophotometry. Three independent batches of minocycline-loaded coacervate were used to make microspheres. An equal number of samples (3) were taken from within each of these batches of the coacervate, small, and large microspheres. This resulted in a total of 9 samples from each batch and an overall total of 27 samples. All samples were then analyzed separately for drug-loading and encapsulation efficiency.

To do this, samples of minocycline-loaded coacervate, small, and large microspheres were collected and freeze-dried for 12 h. The dry-weight of the samples was obtained.

Samples were then dissolved in 200 mM EDTA and analyzed via UV/VIS spectrophotometry (400 nm) to determine the amount of minocycline within each sample.

Drug loading (%)=mass of minocycline (mg)/mass of microspheres (mg)×100

Encapsulation efficiency (%)=% of minocycline in coacervate/% of minocycline in microspheres× 100

Release Profile Analysis

Due to a limited quantity of both small and large microspheres, the three batches of microspheres from the drug-loading study were combined. This resulted in 1 sample of small microspheres and 1 sample of large microspheres. Drug loading of these new samples of microspheres was then carried out as above with two alterations in the procedure: (1) the background solution was a 4:1 mixture of 0.1M Tris-buffer and 200 mM EDTA. This ratio was maintained during the elution trial to ensure there was no calcium polyphosphate precipitate (cloudiness) that may interfere with the spectrophotometric analysis of minocycline. (2) The wavelength used for spectrophotometric analysis was 325 nm instead of 400 nm. This new wavelength was used because it was found to provide stable absorbance readings of minocycline over 7 days.

Two separate elution trials were carried out. In the first elution trial large and small microspheres were separated into 8 samples (4 large, 4 small). Due to a limitation in the quantity of small microspheres, in the second elution trial only large microspheres were used (4 samples). Elution trials were carried out as follows. Microspheres were freeze-dried for 19.5 h. Freeze-dried samples were placed into dialysis tubing, weighed, and both ends were then tied off. Samples within the dialysis tubing were placed into 5 mL of 0.1M Tris-buffer solution, and stored at 37 degrees Celsius with constant agitation (100 oscillations per minute). The dialysis tubing containing the samples were removed and placed into fresh solution at 3, 6, 12, 24, 48, 72, 120, and 168 h intervals. Spectrophotometric analysis was of 3, 6, 12, and 24 hour samples was carried out at 24 hours; 48 and 72 hour samples at 72 hours; and 120 and 168 hour samples at 168 hours. After the 168 h interval, samples were placed into a 4:1 0.1M Tris-buffer to 200 mM EDTA solution for 12 hours to dissolve any remaining samples. A final spectrophotometric analysis was carried out on day 8 to account for any remaining minocycline in the samples.

Elution trials 1 and 2 followed the same procedure with one exception. In elution trial 2, samples were manipulated at time points prior to 48 hours in order to flatten or separate the coacervate, increasing the surface area.

Results

Particle Physical Characteristics

SEM images of minocycline-loaded CPP microspheres are shown in FIGS. 12A-12F. Microspheres in both "small" and "large" groups have a similar morphology; a smooth outer surface with a regular spherical shape. Microspheres from the "large" sample appear significantly larger than those in the "small" sample. The particle size distribution within the "large" microspheres was as follows: 10% were below 86.9+/−3.85 um (D10), 50% were less than 181+/−4.22 um (D50), and 90% were less than 317+/−8.66 um (D90) (Table 4). The particle size distribution within the "small" microspheres was as follows: 10% were below 8.76+/−0.16 um (D10), 50% were less than 18.5+/−0.314 um (D50), and 90% were less than 42.1+/−3.41 um (D90) (Table 5). The corresponding distributions are shown graphically as well (FIGS. 13A and 13B).

As shown in FIGS. 12A-12F, minocycline loaded calcium polyphosphate microspheres appear spherical. Small microspheres (left) and large microspheres (right) are shown with (from top to bottom) 50, 100, and 500 um scales.

TABLE 4

Particle size analysis of "large" calcium polyphosphate microspheres loaded with minocycline. The sample of calcium polyphosphate microspheres were suspended in ethylene glycol and analyzed using laser diffraction (Malvern Mastersizer 3000). 20 trials were carried out on the same sample.

| | Dx (10) (μm) | Dx (50) (μm) | Dx (90) (μm) | Dx (00) (μm) | Dx (100) (μm) |
|---|---|---|---|---|---|
| Mean (μm) | 86.9 | 181 | 317 | 21.3 | 539 |
| Standard deviation (μm) | 3.85 | 4.22 | 8.66 | 0.0274 | 33.6 |
| 1RSD (%) | 4.43 | 2.33 | 2.73 | 0.129 | 6.24 |

FIG. 13A shows the particle size distribution of "large" calcium polyphosphate microspheres loaded with minocycline based on 20 trials using the same sample. Microspheres were placed into ethylene glycol and analyzed using laser diffraction (Malvern Mastersizer 3000)

FIG. 13B shows the particle size distribution of "small" calcium polyphosphate microspheres loaded with minocycline based on 23 trials using the same sample. Microspheres were placed into ethylene glycol and analyzed using laser diffraction (Malvern Mastersizer 3000).

TABLE 5

Particle size analysis of "small" calcium polyphosphate microspheres loaded with minocycline. The sample of calcium polyphosphate microspheres were suspended in ethylene glycol and analyzed using laser diffraction (Malvern Mastersizer 3000). 23 trials were carried out on the same sample.

| | Dx (10) (μm) | Dx (50) (μm) | Dx (90) (μm) | Dx (00) (μm) | Dx (100) (μm) |
|---|---|---|---|---|---|
| Mean (μm) | 8.76 | 18.5 | 42.1 | 3.21 | 80 |
| Standard deviation (μm) | 0.16 | 0.314 | 3.41 | 0.161 | 10.4 |
| 1RSD (%) | 1.83 | 1.69 | 8.1 | 5.01 | 13 |

Drug Loading

The highest mean drug loading (%) of calcium polyphosphate was observed in the coacervate (1.64%), followed by the large microspheres (1.17%), and the lowest was observed in the small microspheres (0.84%) (Table 6). Large microspheres had an encapsulation efficiency of 72.7% while small microspheres had an encapsulation efficiency of 50.9% (Table 5). While large microspheres had higher drug loading and encapsulation efficiency versus small microspheres, they also had higher variability (Table 6).

TABLE 6

Mean Drug loading (%) and Encapsulation efficiency (%) of minocycline using calcium polyphosphate.

| | Drug loading (%) | Encapsulation efficiency (%) |
|---|---|---|
| Coacervate | 1.64 ± 0.16 | |
| Small microspheres | 0.84 ± 0.14 | 50.9 ± 3.86 |
| Large microspheres | 1.17 ± 0.28 | 72.7 ± 15.5 |

Elution Studies—Trial 1

Drug loading of the combined sample of large microspheres was 1.7% while the combined small microsphere sample was 1.1% (Table 7). These drug loading values were increased compared to the mean drug loading described previously for the separated small and large samples of microspheres (Table 6).

TABLE 7

Raw data determining mean drug loading of minocycline into calcium polyphosphate microspheres.

| Sample | Dry weight (mg) | [minocycline] (mg/mL) | Minocycline (mg) | Mg of minocycline per mg of microspheres | Mean ($mg_{minocycline}$/ $mg_{micro-spheres}$) | Mean drug loading (%) |
|---|---|---|---|---|---|---|
| A | 19.3 | 0.090 | 0.224 | 0.012 | | |
| B | 25.8 | 0.121 | 0.303 | 0.012 | | |
| C | 30.4 | 0.122 | 0.306 | 0.010 | 0.011 | 1.1 |
| D | 23.3 | 0.187 | 0.469 | 0.020 | | |
| E | 28.7 | 0.182 | 0.454 | 0.016 | | |
| F | 30.0 | 0.177 | 0.442 | 0.015 | 0.017 | 1.7 |

Figure 14:
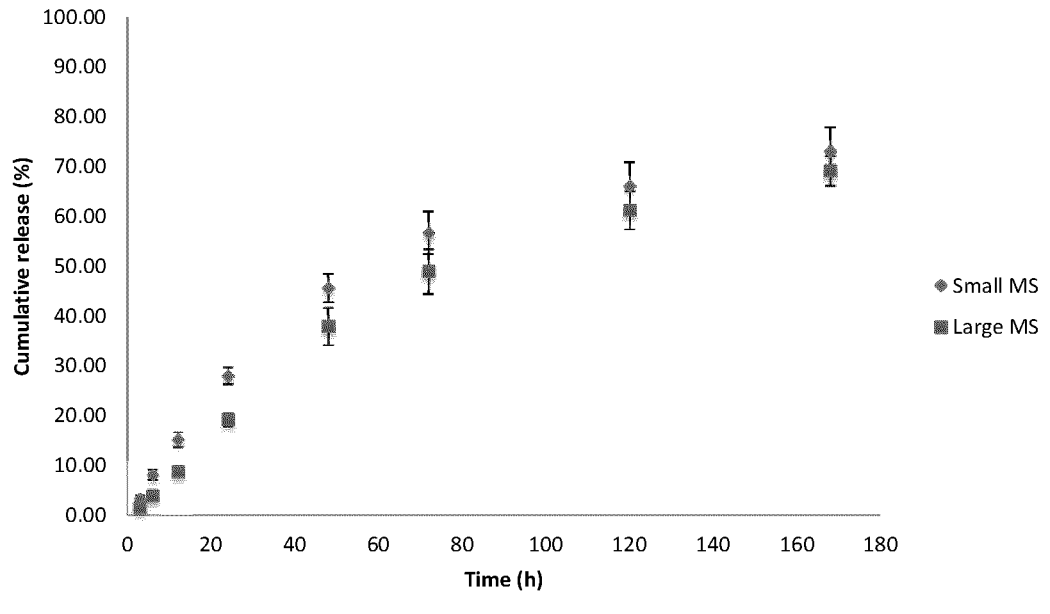
FIG. 14 depicts a graph representing the mean cumulative release of minocycline from small and large calcium polyphosphate microspheres.

Drug release was observed over 7 days. Mean cumulative release of minocycline from small and large calcium polyphosphate microspheres are shown in FIG. 14. Microspheres were placed into 0.1M Tris-buffer solution for 7 days at 37° C. with constant agitation.

Within the first 3 hours of placing the microspheres into the elution medium (0.1M Tris-buffer), the microspheres aggregated and formed a coacervate. This coacervate was yellow in color, with no appreciable change until 24 hours; at this point some fading of the yellow color was observed. The reduction in yellow color, as well as a reduction in the coacervate size, continued gradually throughout the observation period. Following the initial 7-day elution trial, small microspheres released 73% and large microspheres released 69% of their calculated total of minocycline as shown in FIG. 14.

The release of minocycline was similar from small and large microspheres; release profiles for both small and large microspheres were curvilinear with an initial linear portion from 3 to 48 hours, followed by a decreased cumulative release between time points 48 and 168 hours.

The observed cumulative drug release over 7 days, plus any minocycline remaining in the sample determined on day 8, was found to be 95% and 86% of the expected release for small and large microspheres, respectively.

Elution Studies—Trial 2

Drug loading for the large microspheres was also determined during the second elution trial of "large" microspheres to be 1.6% (Table 8)

TABLE 8

Raw data determining average drug loading of minocycline into large calcium polyphosphate microspheres.

| Sample | Dry weight (mg) | [mino-cycline] (mg/mL) | Mino-cycline (mg) | Mg of minocycline per mg of microspheres | Mean ($mg_{minocycline}$/ $mg_{microspheres}$) |
|---|---|---|---|---|---|
| A | 15.4 | 0.060 | 0.242 | 0.016 | |
| B | 15.5 | 0.060 | 0.242 | 0.016 | 0.016 |

Figure 15:
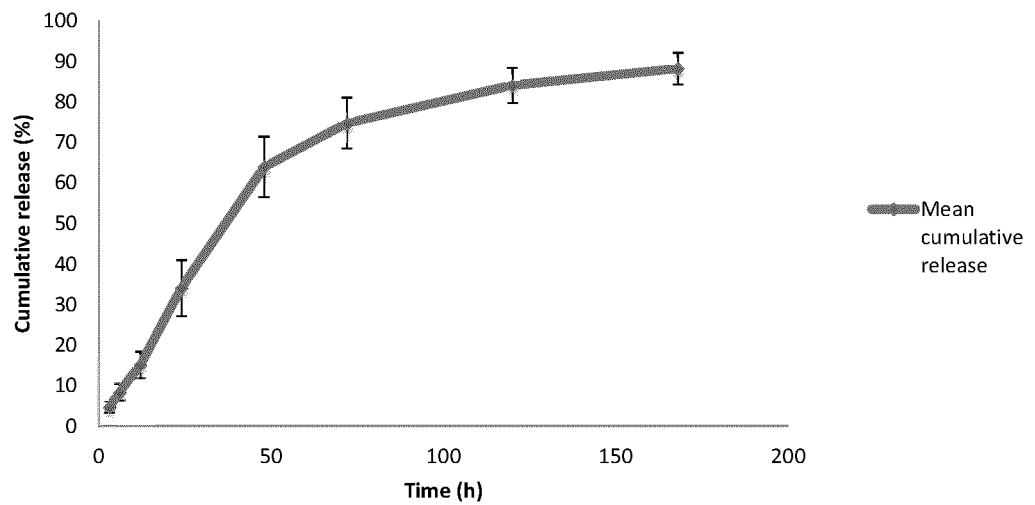
FIG. 15 depicts a graph representing the mean cumulative release of minocycline from large calcium polyphosphate microspheres.

In the second elution trial a similar release profile was observed (FIG. 15). Here, the mean cumulative release of minocycline from large calcium polyphosphate microspheres was determined. Microspheres were placed into 0.1M Tris-buffer solution for 7 days at 37° C. with constant agitation. Microspheres were further agitated by manually breaking up coacervate at 24 and 48 hours. However there was an increase in cumulative release with the first 48 hours compared to the initial elution trial as shown in FIG. 14.

Following the second 7-day elution trial, 88% of the total calculated minocycline had been released (See FIG. 15).

What is claimed is:

1. A method for preparing spherical phosphate glass microspheres, the method comprising:
  (a) providing a phosphate polymer comprising a linear polymer of phosphate having a degree of polymerization ranging from about 3 to about 20,000;
  (b) preparing a coacervate comprising admixing an aqueous solution of the phosphate polymer with metal cations thereby forming a polyphosphate coacervate the metal cations selected from the group consisting of: $Ag^+$, $Zn^{2+}$, $Tc^{4+}$, $Gd^{3+}$, $Ga^{3+}$, $La^{3+}$, $Ca^{2+}$, $Cu^{2+}$, $Mg^{2+}$, $Sr^{2+}$, $Fe^{2+}$, $Y^{3+}$, $Ba^{2+}$ or combinations thereof;
  (c) admixing the polyphosphate coacervate with a water immiscible organic solvent to transform the polyphosphate coacervate into spherical particles;
  (d) solidifying the spherical particles using a solvent extraction process, to form the polyphosphate glass microspheres; and;
  (e) dehydrating the polyphosphate glass microspheres by admixing the polyphosphate glass microspheres of step (d) with a water immiscible solvent.

2. The method according to claim 1, wherein the phosphate polymer is a sodium polyphosphate polymer selected from the group consisting of: Graham salt, and sodium polymetaphosphate.

3. The method according to claim 1, wherein the phosphate polymer is a monovalent polyphosphate or a polyphosphoric acid.

4. The method according to claim 3, wherein the monovalent phosphate polymer is a sodium polyphosphate polymer selected from the group consisting of: Graham salt, sodium polymetaphosphate and combinations thereof.

5. The method according to claim 1, wherein the metal cation is a monovalent cation, a multivalent cation, an organic cation, or combinations thereof.

6. The method according to claim 1, wherein the water immiscible solvent of step (c) comprises chloroform or dichloromethane.

7. The method according to claim 1, wherein the step (d) solvent extraction process comprises mixing the spherical particles with a water-miscible solvent that is also miscible with the organic solvent in step (c).

8. The method according to claim 1, wherein the dehydrating step (e) comprises isolating the polyphosphate glass microspheres of step (d) and washing the polyphosphate glass microspheres one or more times with chloroform or dichloromethane and then one or more washes in a water-immiscible solvent.

* * * * *

UNITED STATES PATENT AND TRADEMARK OFFICE
CERTIFICATE OF CORRECTION

| | | |
|---|---|---|
| PATENT NO. | : 12,145,875 B2 | Page 1 of 1 |
| APPLICATION NO. | : 15/762790 | |
| DATED | : November 19, 2024 | |
| INVENTOR(S) | : Mark Filiaggi and Arash Momeni | |

It is certified that error appears in the above-identified patent and that said Letters Patent is hereby corrected as shown below:

In the Claims

At Claim 1, Column 40, Lines 26-28 the following paragraph should be deleted: "(a) providing a phosphate polymer comprising a linear polymer of phosphate having a degree of polymerization ranging from about 3 to about 20,000;";
At Claim 1, Column 40, Lines 29: "(b)" should read --(a)--;
At Claim 1, Column 40, Line 30: "the phosphate polymer" should read --a linear polymer of phosphate having a degree of polymerization ranging from about 3 to about 20,000--;
At Claim 1, Column 40, Line 31: "," should be added after "coacervate";
At Claim 1, Column 40, Line 34: "or combinations thereof" should read --and combinations thereof--;
At Claim 1, Column 40, Line 35: "(c)" should read --(b)--;
At Claim 1, Column 40, Line 38: "(d)" should read --(c)--;
At Claim 1, Column 40, Line 41: "(e)" should read --(d)--;
At Claim 1, Column 40, Line 43: "(d)" should read --(c)--;
At Claim 6, Column 40, Line 59: "(c)" should read --(b)--;
At Claim 7, Column 40, Line 61: "(d)" should read --(c)--;
At Claim 7, Column 40, Line 64: "(c)" should read --(b)--;
At Claim 8, Column 40, Line 66: "(e)" should read --(d)--;
At Claim 8, Column 40, Line 67: "(d)" should read --(c)--.

Signed and Sealed this
Fifth Day of August, 2025

Coke Morgan Stewart
*Acting Director of the United States Patent and Trademark Office*